US007919081B2

(12) United States Patent
Maier et al.

(10) Patent No.: US 7,919,081 B2
(45) Date of Patent: Apr. 5, 2011

(54) HYDROGENASE DEFICIENT BACTERIAL STRAINS

(75) Inventors: Robert J. Maier, Athens, GA (US); John S. Gunn, Powell, OH (US)

(73) Assignee: University of Georgia Research Foundation, Inc., Athens, GA (US)

( * ) Notice: Subject to any disclaimer, the term of this patent is extended or adjusted under 35 U.S.C. 154(b) by 540 days.

(21) Appl. No.: 10/591,203

(22) PCT Filed: Feb. 28, 2005

(86) PCT No.: PCT/US2005/006638

§ 371 (c)(1),
(2), (4) Date: Jun. 22, 2007

(87) PCT Pub. No.: WO2005/086669

PCT Pub. Date: Sep. 22, 2005

(65) Prior Publication Data

US 2009/0081257 A1 Mar. 26, 2009

Related U.S. Application Data

(60) Provisional application No. 60/549,306, filed on Mar. 2, 2004, provisional application No. 60/604,846, filed on Aug. 26, 2004.

(51) Int. Cl.

| | |
|---|---|
| ***A01N 63/00*** | (2006.01) |
| ***A61K 48/00*** | (2006.01) |
| ***A61K 39/00*** | (2006.01) |
| ***A61K 39/02*** | (2006.01) |
| ***C12N 1/20*** | (2006.01) |
| ***C12N 15/87*** | (2006.01) |

(52) U.S. Cl. ................. 424/93.48; 424/93.2; 424/200.1; 424/184.1; 424/234.1; 435/252.8; 435/461; 435/879

(58) Field of Classification Search ........................ None
See application file for complete search history.

(56) References Cited

U.S. PATENT DOCUMENTS 3,651,214 A * 3/1972 Raettig ...................... 424/203.1

OTHER PUBLICATIONS

Sawers et al. J. Bacteriol. 168: 398-404, 1986.*
Kim et al. Appl. Environ. Microbiol. 62: 1759-1763, 1996.*
Schlecht et al. Naturwissenschaften 80: 9-17, 1993, abstract.*
Olson, Jonathan W., et al "Requirement of Nickel Metabolism Proteins HypA and HypB for Full Activity of Both Hydrogenase and Urease in *Helicobacter pylori*" Molecular Microbiology (2001) 39(1), 176-182.
PCT International Search Report for PCT/US2005/006638 completed by the United States Searching Authority on Feb. 1, 2006.
Adams et al. 1981. "Hydrogenase." *Biochim. Biophys. Acta*. 594:105-176.
Adams. (Ed). "Enzymes and proteins from hyperthermophilic microorganisms; Advances in protein chemistry." vol. 48. *Academic Press*, San Diego, CA. 1996. Title Page, Table of Contents.
Albracht et al. "Mechanism of Hydrogen Activation," 2003. (Eds), *Biochemistry and Physiology of Anaerobic Bacteria*. Springer-Verlag, New York, 2003. pp. 20-34 and Table of Contents.
Alper. Apr. 2003. "Putting an Exotic Enzyme together." *ASM News*, 69:170-171. Available online [retrieved on Aug. 16, 2010]. Retrieved from the Internet at: <http://forms.asm.org/microbe/index.asp?bid=14506>; 2 pgs.
Andrews et al. 1997. "A 12-cistron *Escherichia coli* operon (hyf) encoding a putative proton-translocating formate hydrogenlyase system." *Microbiology*. 143:3633-3647.
Black et al. 1994. Sequences and characterization of *hupU* and *hupV* genes of *Bradyrhizobium japonicum* encoding a possible nickel-sensing complex involved in hydrogenase expression. *J. Bacteriol.* 176:7102-7108.
Blaser. "*Helicobacter pylori* and gastric diseases." Clinical Review. BMJ. 1998. 316:1507-1510.
Bock et al., "Fermentation," Chapter 18 in *Escherichia coli and Salmonella typhimurium*; Vo. 1, ASM Press, Washington, D.C. 2002; F.C. Neidhardt et al. (Eds). Available online at: <http://www.ecosal.org/pdf/ecosal-chapter-18.pdf>.
Bond et al. 1975. "Investigation of small bowel transit time in man utilizing pulmonary hydrogen ($H_2$) measurements." *J. Lab. Clin. Med.* 85:546-555.
Boyer et al. 2002. "Acquition of Mn(II) in addition to Fe(II) is required for full virulence of *Salmonella enterica* serovar typhimurium". *Infect. Immun.* 70:6032-6042.
Brown et al. 1987. "Adaption of hydrogen analysis to measure stomach to caecum transit time in the rat." *Gut*. 28:849-854.
Casalot et al. 2001. "Maturation of the [NiFe] hydrogenases." Review. *Trends in Microbiology*. 9(5):228-237.
Cummings. "Fermentation in the human large intestine: evidence and implication for health." 1983. *Lancet 1* 1206:1209.
Datsenko et al. 2000. "One-step inactivation of chromosomal genes in *Escherichia coli* K-12 using PCR products." *Proc. Natl. Acad. Sci. USA*. 97(12):6640-6645.
de Bruyn et al. 2000. Best Practice. Clinical Evidence. "Infectious Disease: Diarrhea." 172:409-412.
Doig et al. 1999. "*Helicobacter pylori* physiology predicted from genomic comparison of two strains." *Microbiol. & Mole. Biol. Rev.* 63(3):657-707.
Ellermeier et al. 2002. "Construction of targeted single copy *lac* fusions using lambda Red and FLP-mediated site-specific recombinationin bacteria." *Gene* 290:153-161.
Ferber et al. 1993. "Hydrogen-ubiquinone oxidoreductase activity by the *Bradyrhizobium japonicum* membrane bound hydrogenase." *FEMS Microbiol. Lett.* 110:257-264.

(Continued)

*Primary Examiner* — S. Devi
(74) *Attorney, Agent, or Firm* — Mueting Raasch & Gebhardt, P.A.

(57) ABSTRACT

The present disclosure describes pathogenic bacteria that have been modified to be deficient in NiFe hydrogenase activity; compositions comprising such modified bacteria, and the use of such bacteria to protect animals from pathogenic enteric bacterial infections.

3 Claims, 4 Drawing Sheets

OTHER PUBLICATIONS

Ferber et al. 1995. "*Bradyrhizobium japonicum* hydrogen-ubiquinone oxidoreductase activity: quinone specificity, inhibition by quinone analogs, and evidence for separate sites of electron acceptor reactivity." *BBA* 1229:334-346.

Florin. 1997. "Alkyl halides, super hydrogen production and the pathogenesis of pneumatosis cystoides coli." *Gut*. 41:778-784.

Fox. "The non-H *pylori* helicobacters: their expanding role in gastrointestinal and systemic diseases." 2002. *Gut*. 50:273-283.

Friedrich et al. 1993. "Molecular biology of hydrogen utilization in aerobic chemolithotrophs." *Annu. Rev. Microbiol*. 47:351-383.

Gunn et al. 2000. "Genetic and functional analysis of a PmrA-PmrB-regulated locus necessary for lipopolysaccharide modification, antimicrobial peptide resistance, and oral virulence of *Salmonella enterica* serovar typhimurium." *Infect. Immun*. 68(11):6139-6146.

Hube et al. "Network of hydrogenase maturation in *Escherichia coli*: role of accessory proteins HypA and HybF." 2002. *J. Bacteriol*. 184(14):3879-3885.

Jamieson et al. 1985. "Effects of anaerobic regulatory mutations and catabolite repression on regulation of hydrogen metabolism and hydrogenase isoenzyme composition in *Salmonella typhimurium*". *J. Bacteriol*. 168(1):405-411.

Jones. 1980. "The role of the membrane-bound hydrogenase in the energy-conserving oxidation of molecular hydrogen by *Escherichia coli." Biochem. J*. 188:345-350.

Keefe et al. 1993. "Purification and characterization of an $O_2$-utilizing cytochrome-c oxidase complex from *Bradyrhizobium japonicum." Biochim. Biophys. Acta*. 1183:91-104.

Kelly et al. 2001. *Helicobacter pylori*, physiology and genetics, *ASM Press*, Washington DC. Title Page, Copyright Page, Table of Contents, and Chapter 10, pp. 113-124.

Kolonay et al. 1994. "Purification and characterization of the cytochrome bd complex from *Azotobacter vinelandii*: Comparison to the complex from *Escherichia coli." J. Bacteriol*. 176(13):4177-4181.

Laurinavichene et al. 2002. "Effect of redox potential on activity of hydrogenase 1 and hydrogenase 2 in *Escherichia coli." Arch. Microbiol*. 178:437-442.

Lemke et al. "Cross-epithelial hydrogen transfer from the midgut compartment drives methanogenesis in the hindgut of cockroaches." *AEM*. 67(10):4657-4661. 2001.

Lifschitz et al. "Carbohydrate digestion in humans from a β-glucan-enriched barley is reduced." 2002. Research Communication. *Human Nutrition and Metabolism, J. Nutr*. pp. 2593-2596.

Maier et al. 1985. "Hydrogen uptake negative mutants of *Rhizobium* and their use in the isolation of *hup* genes." *Methods Enzymol*. 118:528-534 (and references therein).

Maier et al. 1988. "Hydrogen-mediated mannose uptake in *Azotobacter vinelandii." J. Bacteriol*. 170(4):1986-1989.

Maier et al. 1996. "Hydrogen uptake hydrogenase in *Helicobacter pylori." FEMS Microbiology Letters*. 141:71-76.

Maier et al. 2002. "Genes and proteins involved in nickel dependent hydrogenase expression." In: Physiology and Biochemistry of Anaerobic Bacteria. Springer-Verlag, New York. Title Page, Table of Contents, and Chapter 16 (pp. 67-83).

Maier et al., 2003 "Availability and Use of Molecular Hydrogen as an Energy Substrate for *Helicobater* Species.". *Microbes Infect*. 5:1159-1163.

Maier et al. 2003. "Hydrogen oxidizing capabilities of *Helicobacter hepaticus* and *in vivo* availability of the substrate."2003. *J. Bacteriol*. 185(8):2680-2682.

Maier et al. (Eds), Biochemistry and physiology of anaerobic bacteria. Springer-Verlag, New York, 2003. Title Page, Copyright Page, Table of Contents, and Chapter 6, pp. 67-84.

Maier et al., 2004. "Respiratory Hydrogen Use by *Salmonella enterica* Serovar Typhimurium Is Essential for Virulence," Infection and Immunity. 72(11):6294-6299.

Maier et al. 2004. "Use of molecular hydrogen as an energy substrate by human pathogenic bacteria". Intl. Hydrogenases Conference 2004. Biochemical Society Transactions (2005) vol. 33, part 1. pp. 83-85.

McClelland et al. 2001. "Complete Genome Sequence of *Salmonella enterica* serovar typhimurium LT2." *Letters to Nature*. 413:852-856.

McCrae et al. 1978. "Properties of the hydrogenase system in *Rhizobium japonicum* bacteroids." *Biochem. Biophys. Res. Commun*. 80(2):384-390.

McGee et al. 1999. "Mechanisms of *Helicobacter pylori* infection: Bacterial Factors." pp. 155-180. In T.U. Westblom, S.J. Czinn, and J.G. Nedrud (eds), Current Topics in Microbiology and Immunology. Gastroduodenal Disease and *Helicobacteri pylori*: Pathophysiology, Diagnos and Treatment. Spring Verlag, Berlin.

Merberg et al. "Regulation of Hydrogenase in *Rhizobium japonicum*: Analysis of Mutants in Regulation by Carbon Substrates and Oxygen." 1986. *Bacteriol*. 156(3):1236-1242.

Miller et al. 1996. "Pathways of acetate, propionate, and butyrate formation by the human fecal microbial flora." *AEM*, 62(5):1589-1592.

Mutaftschiev et al. 1983. "Hydrogen oxidation activity in membranes from *Rhizobium japonicum." Biochim. Biophys. Acta*. 722:372-380.

Noether. 1971. "Introduction to Statistics: a Fresh Approach." Houghton Mifflin, Boston. Title Page, Table of Contents, and Chapter 14 (pp. 130-142).

Olczak et al. 2002. "Oxidative Stress Resistance Mutants of *Helicobacter pylori." J. Bacteriol*. 184(12):3186-3193.

Oleson et al. 1997. "Maldigestion and colonic fermentation of wheat bread in humans and the influence of dietary fat." *Am. J. Clin. Nutr*. 66:62-66.

Olson et al. 1997. "The HypB protein from *Bradyrhizobium japonicum* can store nickel and is required for the nickel-dependent transcriptonal regulation of hydrogenase." *Mol. Microbiol*. 24(1):119-128.

Olson et al. 2002. "Molecular hydrogen as an energy source for *Helicobacter pylori", Science*. 298:1788-1790.

Pihl et al. 1992. Hydrogen-oxidizing electron transport components in the hyperthermophilic archaebacterium *Pyrodictium brockii. J. Bacteriol*. 174(1):137-143.

Reissmann et al. 2003. "Taming of a poison: biosynthesis of the NiFe-hydrogenase cyanide ligands." *Science*. 299:1067-1070.

Salyers et al. 2002. Bacterial Pathogenesis: A molecular approach. *ASM Press*, Washington, DC. Title Page, Copyright Page, Table of Contents. 10 pgs.

Santos et al. 2001. "Animal models of *Salmonella* infections: enteritis versus typhoid fever". *Micro. Infect*. 3:1335-1344.

Sawers et al. 1985. "Differential Expression of Hydrogenase Isoenzymes in *Escherichia coli* K-12: Evidence for a Third Isoenzyme." *J. Bacteriol*. 164(3):1324-1331.

Smith et al. 2000. "Characteristics of the aerobic respiratory chains of the microaerophiles *Campylobacter jejuni* and *Heliocobacter pylori." Arch Microbiol*. 174:1-10.

Stults et al. 1984. "Nickel is a component of hydrogenase in *Rhizobium japonicum." J. Bacteriol*. 159(1):153-158.

Solnick et al. 2001. "Emergence of diverse *Helicobacter* species in the pathogenesis of gastric and enteropepatic diseases." *Clin. Microbiol*. Rev. 14(1)59-97.

Tamayo et al. 2002. "Identification and Genetic Characterization of PmrA-Regulated Genes and Genes Involved in Polymyxin B Resistance in *Salmonella enterica* Serovar Typhimurium." Infect. Immun. 70(60):6770-6678.

Tharanathan. "Food-derived carbohydrates-structural complexity and functional diversity."2002. *Crit. Rev. Biotechnol*. 22(1):65-84.

Touati et al. 2003. "Chronic *Helicobacter pylori* infections induce gastric mutations in mice." *Gastroenterology* 124. 1408-1419.

Vignais et al. 2001. "Classification and phylogeny of hydrogenases." *FEMS Microbiol. Rev*. 25:455-501.

Wang et al. 1991."Construction of versatile low-copy-number vectors for cloning, sequencing and gene expression in *Escherichia coli*." *Gene* 100:195-199.

Wang. "Amperometric Hydrogen Electrode." *Methods. Enzymol.* 69:409-413.

Wolin et al. 1994. Acetogenesis from CO2 in the Human Colonic Ecosystem, in Acetogenesis, Drake, HL, Ed. Chapman & Hall, New York, Title Page, Table of Contents, and Chapter 11 (pp. 365-385).

Wong et al. 1984. "Hydrogen-oxidizing electron transport components in nitrogen-fixing *Azotobacter vinelandii*." *J. Bacteriol.* 159(1):348-352.

Zhang et al. 2003. "Molecular pathogenesis of *Salmonella enterica* serotype typhimurium-induced diarrhea," *Infect. Immun.* 71(1):1-12.

* cited by examiner

Step 1. PCR amplify FRT-flanked resistance gene

Step 2. Transform strain expressing λ Red recombinase

Step 3. Select antibiotic-resistant transformants.

Step 4. Eliminate resistance cassette using a FLP expression plasmid

SEQUENCE LISTING

```
<160> NUMBER OF SEQ ID NOS: 21

<210> SEQ ID NO 1
<211> LENGTH: 51
<212> TYPE: DNA
<213> ORGANISM: Salmonella typhimurium

<400> SEQUENCE: 1

tagtggtttg ggataaacgt tatgcaaaca gtgtaggctg gagctgcttc g              51


<210> SEQ ID NO 2
<211> LENGTH: 50
<212> TYPE: DNA
<213> ORGANISM: Salmonella typhimurium

<400> SEQUENCE: 2

attgagacct ccgaatcgtc gtcatcgtac catatgaata tcctccttag               50


<210> SEQ ID NO 3
<211> LENGTH: 51
<212> TYPE: DNA
<213> ORGANISM: Salmonella typhimurium

<400> SEQUENCE: 3

tcgtaacgga ataactataa aatgtgtgca gtgtaggctg gagctgcttc g              51


<210> SEQ ID NO 4
<211> LENGTH: 50
<212> TYPE: DNA
<213> ORGANISM: Salmonella typhimurium

<400> SEQUENCE: 4

cccctaagac taatatccgc attacaaaac catatgaata tcctccttag               50


<210> SEQ ID NO 5
<211> LENGTH: 51
<212> TYPE: DNA
<213> ORGANISM: Salmonella typhimurium

<400> SEQUENCE: 5

aaaggagaaa aaatacgcgt tatgaataac gtgtaggctg gagctgcttc g              51


<210> SEQ ID NO 6
<211> LENGTH: 50
<212> TYPE: DNA
<213> ORGANISM: Salmonella typhimurium

<400> SEQUENCE: 6

atcgttcttt tccttaacgc ttagcgtacc catatgaata tcctccttag               50
```

<210> SEQ ID NO 7
<211> LENGTH: 232
<212> TYPE: DNA
<213> ORGANISM: Salmonella typhimurium

<400> SEQUENCE: 7
gcgtcggcaa tgatcaaatg atcacgattc gccatatcgc caagaagttc cattcccgcc 60
acaatacgca ccccgatggc ttcatcggtc agcaaaatat tgccgacccc taagactaat 120
atccgcatta caaaactgca caaagcttca tgaaatcacg acggttaatg ccgtgagaag 180
tgatgagagt attatctcca gtcattttat agttattccg ttacgaagac ct 232

<210> SEQ ID NO 8
<211> LENGTH: 518
<212> TYPE: DNA
<213> ORGANISM: Salmonella typhimurium

<400> SEQUENCE: 8
gtactcattg ccgacacatg cccagtaaat acgaaacagc agcgcgacag taaaaatata 60
cgccgtggta aaatggatca gtcgtatcca gcccatccaa aacataaagg tcgcttcacc 120
ttgaatcgat ggcagggggc ggccaatgaa atatcctgta acagccagga cgacaatgga 180
taacgccgtg atccagtgcc ataaacggac cggcgcttca tagatatagt acccctggct 240
ggttatttct ttgagatgca ttgagacctc cgaatcgtcg tcatcgtact gtttgcataa 300
cgtttatccc aaaccactat agttagtgtg ggcatcatat gttgcatttc ttgtctttct 360
caacgtgttt tagtagcaat tatgtttcta attcgtaaca actgattaca tgtgtgctac 420
tcacattact caaaaacata aattaattta atgttattgg tgatgttgag taaatatagc 480
gttgtgatgg catctcttaa tgttgataag aaaccgtg 518

<210> SEQ ID NO 9
<211> LENGTH: 333
<212> TYPE: DNA
<213> ORGANISM: Salmonella typhimurium

<400> SEQUENCE: 9
cttatcgtta atccgatacg ctttttttcac attatttctg gcggtatacg ccggtgcaaa 60
gtgaatcggg ctcgtttccg cgctcgcgcg taacacaatg atttaccttg ctggcggaac 120
gtcaacggac ccgcaaaagc gccttatgcc cctggcggag cgtggtgcaa aaaggagaaa 180
aaatacgcgt tatgaataac ggtacgctaa gcgttaagga aaagaacgat gactggaaag 240
ctatctccac gcgtcgggga ggcgcgtgat actgccgtca gccactatgt gtttgaagcg 300
ccggtacgcc tgtggcactg gctaacggtg gcc 333

<210> SEQ ID NO 10
<211> LENGTH: 19
<212> TYPE: DNA
<213> ORGANISM: Salmonella typhimurium

<400> SEQUENCE: 10
cacggtttct tatcaacat 19

<210> SEQ ID NO 11
<211> LENGTH: 20
<212> TYPE: DNA
<213> ORGANISM: Salmonella typhimurium

<400> SEQUENCE: 11

-continued gtactcattg ccgacacatg 20

<210> SEQ ID NO 12
<211> LENGTH: 20
<212> TYPE: DNA
<213> ORGANISM: Salmonella typhimurium

<400> SEQUENCE: 12
ccgggatggc ggttcgcttc 20

<210> SEQ ID NO 13
<211> LENGTH: 20
<212> TYPE: DNA
<213> ORGANISM: Salmonella typhimurium

<400> SEQUENCE: 13
gcgtcggcaa tgatcaaatg 20

<210> SEQ ID NO 14
<211> LENGTH: 21
<212> TYPE: DNA
<213> ORGANISM: Salmonella typhimurium

<400> SEQUENCE: 14
cttatcgtta atccgatacg c 21

<210> SEQ ID NO 15
<211> LENGTH: 20
<212> TYPE: DNA
<213> ORGANISM: Salmonella typhimurium

<400> SEQUENCE: 15
ggccaccgtt agccagtgcc 20

<210> SEQ ID NO 16
<211> LENGTH: 24
<212> TYPE: DNA
<213> ORGANISM: Salmonella typhimurium

<400> SEQUENCE: 16
gctctagaaa aaatacgcgt tatg 24

<210> SEQ ID NO 17
<211> LENGTH: 25
<212> TYPE: DNA
<213> ORGANISM: Salmonella typhimurium

<400> SEQUENCE: 17
cccaagctta gcgtacctgg acggc 25

<210> SEQ ID NO 18
<211> LENGTH: 24
<212> TYPE: DNA
<213> ORGANISM: Helicobacter hepaticus

<400> SEQUENCE: 18
ttcgtggtat gaggataatc agcc 24

<210> SEQ ID NO 19
<211> LENGTH: 24
<212> TYPE: DNA
<213> ORGANISM: Helicobacter hepaticus

<400> SEQUENCE: 19

-continued

```
aataaagcac aactcccgtg agag                                              24


<210> SEQ ID NO 20
<211> LENGTH: 23
<212> TYPE: DNA
<213> ORGANISM: Helicobacter hepaticus

<400> SEQUENCE: 20

ggctagatac aagaatcgct aat                                               23


<210> SEQ ID NO 21
<211> LENGTH: 23
<212> TYPE: DNA
<213> ORGANISM: Helicobacter hepaticus

<400> SEQUENCE: 21

ctacctacta ccgcataatc aag                                               23
```

HYDROGENASE DEFICIENT BACTERIAL STRAINS

CROSS-REFERENCE TO RELATED APPLICATIONS

This application is a U.S. national counterpart application, filed under 35 U.S.C. §371, of international application serial No. PCT/US2005/006638 filed Feb. 28, 2005, which claims the benefit of U.S. Provisional Application Ser. No. 60/549,306, filed Mar. 2, 2004, and 60/604,846, filed Aug. 26, 2004, each of which is incorporated herein by reference.

BACKGROUND

Together enteric pathogens are responsible for an estimated 2 million deaths annually and cause millions more cases of diarrheal illness annually, even in developed countries. *S. typhimurium* is one of the most common causes of diarrhea and is transmitted primarily by ingestion of contaminated food. Although the infected individual typically recovers from the abdominal pain and diarrhea, an individual will continue to shed *S. typhimurium* for up to three months, and in some individuals for up to a year after the initial symptoms. Therefore it is clear the bacteria have the capability of surviving and growing in the host.

Based on annotated whole genome sequences, intestinal disease-causing bacteria such as *Salmonella, Escherichia coli, Shigella, Yersinia*, and *Campylobacter* all contain homologous hydrogenases. Hydrogenases are membrane associated "$H_2$ splitting" enzymes, that carry out the following relatively simple $H_2$ oxidizing reaction: $H_2^-$=>$2e^-+2H^+$. Metal containing hydrogenases are subdivided into three classes: Fe ("iron only") hydrogenases, Ni—Fe hydrogenases and Ni—Fe—Se hydrogenases. The membrane-bound hydrogenases associated with $H_2$ oxidation typically split molecular $H_2$ via the NiFe metal center, with the release of protons and low potential electrons (see Vignais, et al., (2001) FEMS Microbiol. Rev. 25:455-501).

The Ni—Fe hydrogenases are heterodimeric proteins consisting of small (S) and large (L) subunits. The small subunit contains three iron-sulphur clusters, two $[Fe_4S_4]^{2+/1+}$ and one $[Fe_3S_4]^{1+/0}$, and the large subunit contains a nickel-iron centre. The hydrogen ($H_2$) splitting reaction by Ni—Fe hydrogenases does not yield energy as ATP per se, but the two protons released from $H_2$ can contribute to a proton gradient across the membrane. Importantly, the NiFe hydrogenase enzymes are membrane associated where the electrons generated from splitting molecular hydrogen are sequentially passed to heme-containing or quinone-reactive proteins. The potential energy thus generated can be used for ATP production via oxidative phosphorylation or to drive carbon transport systems.

Only recently has the process of energy generation from $H_2$ been recognized as being potentially important for bacterial pathogenesis within animal hosts (Olson and Maier (2002) Science. 298:788-1790). Hydrogen is present in animal's digestive tract as a consequence of the fermentive metabolism by the normal colonic flora. Therefore, the possession of hydrogenase enzymes by enteric bacterial strains, together with a readily available source of $H_2$ in the digestive tract, may play an important role in enteric bacteria's ability to proliferate in the digestive tract of an animal.

One aspect of the present disclosure relates to compositions and a method of reducing the virulence of pathogenic bacteria by preventing the expression of functional hydrogenase activity in the bacteria.

SUMMARY OF VARIOUS EMBODIMENTS OF THE DISCLOSURE

One embodiment of the present disclosure is directed to an isolated bacterium that has been modified to be hydrogenase deficient relative to wild type strains. More particularly, the modified bacterial strain has a greater than 50% reduction in hydrogenase activity relative to a wild type stain. More particularly, in one embodiment the modified strain is incapable of expressing a functional NiFe hydrogenase protein. In accordance with one embodiment the bacterial strain is an enteric pathogen selected from the group consisting of *Salmonella, E. Coli, Shigella*, and *Campylobacter* (including for example, *Salmonella typhimurium, Salmonella typhi, E. Coli* 0157, *Shigella flexneri, Shigella sonnei*, and *Campylobacter jejuni*), wherein the strain comprises a mutation to each of the NiFe hydrogenase genes present in the genome of the strain, such that the mutations prevent the expression of a functional NiFe hydrogenase protein.

The present disclosure further encompasses compositions that comprise the novel hydrogenase deficient strains described herein. These compositions may include a pharmaceutically acceptable carrier, adjuvants, other beneficial bacterial strains (i.e. probiotics) or other antimicrobial agents. The compositions are formulated for admission to a warm blooded vertebrate, either orally or peritoneally. In one embodiment the hydrogenase deficient bacterial compositions are in the form of a frozen or lyophilized powder. Alternatively they can be combined with the food or drinking water of the animal to which they are to be administered.

The present disclosure is also directed to the use of compositions comprising hydrogenase deficient bacteria to treat or prevent enteric bacterial pathogenic infections. In one embodiment a method of inducing an immune response in a mammal against a pathogenic bacterium is provided, wherein the immune response protects the animal from, or reduces the severity of, future infections of that pathogen. The method comprises the step of administering to said mammal a composition comprising live bacterium, wherein the bacterium has been modified to prevent the expression of a functional NiFe hydrogenase protein. In one embodiment the bacterium is selected from the group consisting of *Salmonella typhimurium, Salmonella typhi, E. Coli* 0157, *Shigella flexneri, Shigella sonnei*, and *Campylobacter jejuni*, and the composition is administered orally.

In one embodiment a method of protecting a warm blooded vertebrate against an infection with pathogenic *Salmonella, Heliobactor, E. coli, Shigella*, or *Campylobacter* is provided. The method comprises the step of administering to the subject a live bacterium, selected from the group consisting of *Salmonella, Heliobactor, E. coli, Shigella*, and *Campylobacter*, wherein the bacterium has been modified to prevent expression of a functional NiFe hydrogenase protein. In one embodiment the pathogenic bacterial strain is modified to have a deletion of at least a portion of each of the NiFe hydrogenase genes present in the pathogenic bacterial strain's genome, rendering the bacterium incapable of expressing detectable amounts of NiFe hydrogenase protein. In one embodiment a composition comprising a live *Salmonella* strain is administered to a mammalian species to protect the species, or at least reduce the severity of symptoms associated with, a *Salmonella* infection. In one embodiment the method comprises administering live *Salmonella* wherein each of the NiFe hydrogenase genes present in the genome of the bacterium has been mutated to prevent expression of a functional NiFe hydrogenase protein.

DETAILED DESCRIPTION OF EMBODIMENTS

Definitions

Figure 1:
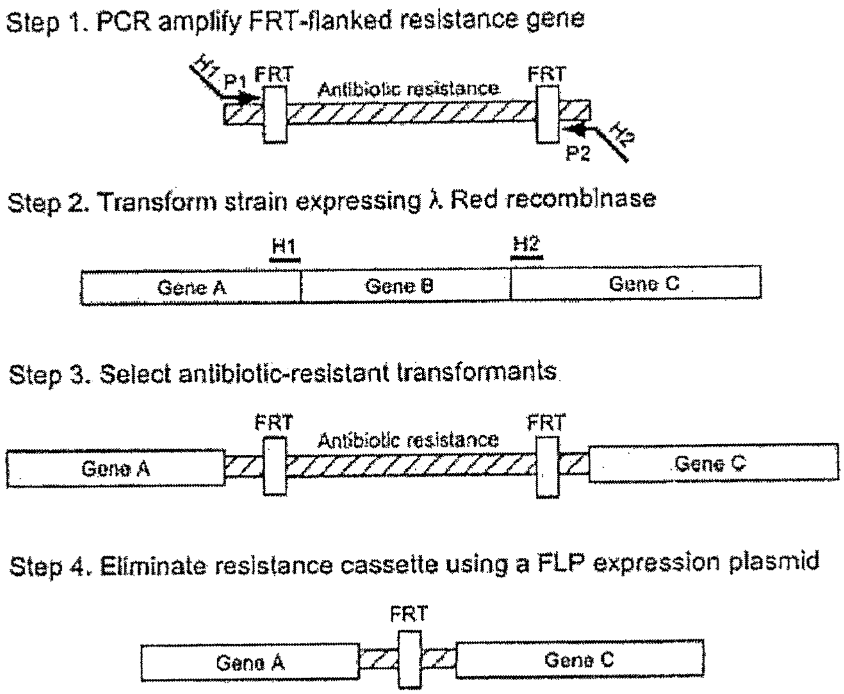
FIG. 1 is a schematic representation of the steps taken to produce the mutant bacteria of the present disclosure.

In describing and claiming the invention, the following terminology will be used in accordance with the definitions set forth below.

The term "isolated" as used herein refers to material that has been removed from its natural environment and separated from other components normally associated with the material in a native environment. For example, a naturally-occurring bacteria present in a living animal is not isolated, but the same bacterial strain, removed from the animal and substantially free of coexisting microorganisms present in the natural system, is isolated.

The term "wild type" refers to an organism that comprises one of the major genotypes of the organism that occurs in nature (i.e. how the organisms are found naturally, in the wild, before being manipulated by researchers), in contrast to an organism containing mutations induced deliberately by man or produced by man using controlled cross-breeding.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes alleviating the symptoms associated with a specific disorder or condition and/or preventing or eliminating said symptoms.

As used herein, the term "hydrogenase deficient bacteria" includes any bacterial strain that expresses substantially reduced hydrogenase activity levels (at least a 33% reduction) relative to a wild type counterpart when both types of cells are cultured under similar conditions.

As used herein, the term "NiFe hydrogenase" refers to a heterodimeric protein that comprises a small (S) and large (L) subunit and a nickel-iron centre. A "functional NiFe hydrogenase" is a NiFe hydrogenase capable of catalyzing the reversible oxidation of molecular hydrogen ($H_2$).

As used herein, the term "hydrogenase gene" refers to any DNA sequence that encodes a protein that comprises a functional hydrogenase enzyme. For example, reference to the "NiFe hydrogenase gene" is intended to include the DNA sequences encoding both the small and the large subunits.

Embodiments

The present disclosure is directed to bacteria, and compositions comprising such bacteria, that have been modified to express reduced hydrogenase activity levels relative to their wild type counterparts when both types of cells are cultured under similar conditions. In one embodiment the bacterial strains are pathogenic enteric strains that have been modified to prevent detectable levels of NiFe protein from being produced by the bacteria. In accordance with one embodiment, compositions comprising the hydrogenase deficient bacteria of the present disclosure are administered to an animal to prevent a pathogenic bacterial infection, or reduce or eliminate the presence of a pathogenic bacterium in an animal.

In one embodiment the hydrogenase deficient bacteria of the present disclosure express less than half the hydrogenase activity levels of a wild type counterpart, and in another embodiment the modified bacteria express less than 25% the hydrogenase activity levels of a wild type counterpart. In another embodiment the modified bacteria express less than 5% of the hydrogenase activity levels of a wild type counterpart. In one embodiment the modified bacteria expresses less than 5% of the NiFe hydrogenase protein than a wild type strain. In another embodiment the modified bacteria expresses undetectable levels of NiFe hydrogenase protein and/or activity.

Bacteria can be modified to decrease their hydrogenase activity (i.e. disrupt the bacteria's ability to oxidize $H_2$) using any of the standard techniques known to those skilled in the art. The NiFe hydrogenase deficient bacterial strains of the present disclosure is intended to encompass all such strains that have been modified to express low or undetectable amounts of NiFe hydrogenase protein and/or activity. For example, the expression or stability of hydrogenase can be decreased through the use of anti-sense nucleic acids, the use of ribozymes and/or by introducing mutations into hydrogenase gene sequences. Mutations of the genes may comprise point mutations, insertions and/or deletions of the hydrogenase gene sequence, provided that the mutation(s) either interfere with the transcription of the gene, interfere with the translation of the gene transcript, or interfere with the function of the encoded protein. In one embodiment one or more mutations are introduced into each of the functional NiFe hydrogenase genes of the target organism, resulting in the organism's failure to produce detectable levels of NiFe hydrogenase protein and/or activity.

In accordance with one embodiment of the present disclosure, a pathogenic bacterial cell is provided wherein the NiFe hydrogenase genes of the bacteria have been modified my mutation to prevent the bacteria from expressing a functional NiFe hydrogenase enzyme. In accordance with one embodiment the mutation introduces one or more stop codons into the reading frame of the NiFe hydrogenase gene. Alternatively, the mutation may introduce a frameshift that allows for the generation of a protein that is devoid of, or has very poor, hydrogenase activity. In another embodiment the mutation comprises a deletion of at least a portion of the gene, rendering the gene incapable of expressing a functional NiFe hydrogenase protein. Since several NiFe hydrogenase genes are expressed from operons that encode several gene products, it is advantageous in these situation to select a mutation strategy that minimizes the impact on downstream gene expression.

In accordance with one embodiment an isolated pathogenic bacterium is provided wherein each of the hydrogenase genes present in the genome of the bacterium is mutated, wherein the mutations prevent the expression of a functional hydrogenase protein. In one embodiment the bacterium is selected from the group consisting of *Salmomella, Heliobactor, Escherichia* (e.g. *E. coli*), *Shigella, Yersinia, Pastuerellaceae*, and *Campylobacter*. More particularly, the bacterium is selected from the group consisting of *Salmonella typhimurium, Salmonella typhi, E. coli* 0157, *Shigella flexneri, Shingella sonnei, H. pylori, H. hepaticus, Actinobacillus pleuropneumoniae* and *Campylobacter jejuni*. In one embodiment the bacterium is *Salmonella typhimurium, Salinonella typhi* or *Campylobacter jejuni*, wherein each of the NiFe hydrogenase genes present in the organism has been mutated to prevent the bacterium from expressing a functional NiFe hydrogenase protein. In one embodiment the mutations to the hydrogenase genes are nonpolar mutations, designed to minimize the affect on the rate of expression of nearby gene products.

In accordance with one embodiment a mutant *Salmonella* strain is provided wherein one or more of its NiFe hydrogenase genes have been mutated to prevent expression of the NiFe hydrogenase gene. In one embodiment the mutant *Salmonella* strain is *Salmonella typhimurium* or *Salmonella typhi* that has three of its NiFe hydrogenase genes mutated to prevent expression of the corresponding gene products. In one embodiment the triple mutant strain comprises deletion mutations made at STM 3147, STM 1538, and STM 1786. Mutant strains at STM numbers (for the large subunit) 3147, 1538, and 1787 correspond to gene designations hybC for S™ 3147, and hydB for the other two sites. In one embodiment the mutations comprise a 4972 bp deletion of the Group I genes (deleting genes STM 3147 through STM 3150) represented by coordinates 3313762 to 3308790 in the TIGR comprehensive microbial resource for *S. typhimurium*; a 2905 bp deletion of the Group II genes (deleting genes STM 1538 and STM 1539) represented by coordinates 1614904 to 1611999 in the TIGR comprehensive microbial resource for *S. typhimurium*; and a 2905 bp deletion of the Group III genes (deleting genes STM 1786 and STM 1787) represented by coordinates 1884828 to 1887733 in the TIGR comprehensive microbial resource for *S. typhimurium*. These deletions remove the genes encoding the large and small subunit of the respective Group I, II and II NiFe hydrogenases.

In accordance with one embodiment a triple mutant *S. typhimurium* strain (JSG 321) is provided wherein the three NiFe hydrogenase genes have been deleted, and the strain comprises contiguous sequences of SEQ ID NO 7, SEQ ID NO: 8 and SEQ ID NO: 9. This triple mutant hydrogenase deficient *S. typhimurium* strain (JSG 321) having the genes STM 3150, STM 3149, STM 3148, STM 3147, STM 1539, STM 1538, STM 1786, and STM 1787 deleted has been deposited in an International Depository Authority in compliance with the Budapest Treaty. In particular *S. typhimurium* strain (JSG 321) has been deposited with the American Type Culture Collection depository (10801 University Blvd, Manassas, Va., 20108, USA), on Feb. 4, 2005 and assigned deposit Accession No: PTA-6556.

The hydrogenase deficient bacteria of the present disclosure can be combined with pharmaceutically acceptable carriers, stabilizing agents, other probiotic organisms or antimicrobial agents to prepare a composition that is effective in preventing or reducing the symptoms associated with *Salmonella, Escherichia* (e.g. *E. coli*), *Shigella, Yersinia, Helicobacter, Pastuerellaceae*, and *Campylobacter* infections. In accordance with one embodiment an antigenic composition comprising a hydrogenase deficient bacterium and a pharmaceutically acceptable carrier is provided. The composition can be administered to a warm blooded vertebrate, including humans, to provide a protective effect in the animal against one or more enteropathogens.

The cultures may be frozen, or freeze dried to form a lyophilized powder, for storage stability and ease of handling. Freeze dried cultures may be directly administered to the warm blooded vertebrates (e.g. humans, or domesticated animals such as poultry, cattle and other farm animals) or in the alternative reconstituted prior to use. In one embodiment the competitive exclusion formulation is encapsulated using techniques conventional in the art, including, but not limited to encapsulation in an alginate gel. The formulation of the hydrogenase deficient bacterial composition will vary depending on the route of administration. In one embodiment the compositions are formulated for oral delivery. In another embodiment the compositions can be formulated for parenteral administration including for example intraperitoneal, subcutaneous, intramuscular, intraspinal, or intravenous routes of administration.

In accordance with one embodiment the hydrogenase deficient bacterial composition is combined with a conventional feed, providing a novel feed product which may be orally ingested by animals. This novel feed product may be prepared by mixing the feed constituents in any conventional fashion for preparing animal feeds. In one embodiment the novel feed composition is prepared by combining a powder form of the hydrogenase deficient bacterial composition with the feed constituents in a commercial mill following a prescribed formulation.

In accordance with one embodiment a composition comprising two or more pathogenic strains selected from the group consisting of *H. Pylori, H. Hepaticus, Salmonella typhimurium, Salmonella typhi, E. Coli* 0157, *Shigella flexneri, Shigella sonnei*, and *Campylobacter jejuni*, wherein each of the NiFe hydrogenase genes of the respective pathogenic strains has been mutated, wherein the mutations prevent expression of a functional NiFe hydrogenase protein.

In accordance with one embodiment of the present disclosure, a method of inducing an immune response in a mammal against a pathogenic bacterium is provided, wherein the immune response protects the animal from, or reduces the severity of, future infections by that pathogen. The method comprises the step of administering to said mammal a composition comprising live bacterium, wherein the bacterium has been modified to prevent the expression of a functional NiFe hydrogenase protein. In one embodiment the bacterium is selected from the group consisting of *Salmonella, E. Coli, Shigella*, and *Campylobacter*. In one embodiment, the bacteria is selected from the group consisting of *Salmonella typhimurium, Salmonella typhi, E. Coli* 0157, *Shigella flexneri, Shigella sonnei*, and *Campylobacter jejuni*, and the composition is administered orally. In one embodiment the immune response is directed against a pathogenic bacterium selected from the group consisting of *Salmonella typhimurium, Salmonella typhi* and *Campylobacter jejuni.*

In one embodiment the method of inducing an anti-pathogen immune response in a mammal comprises the step of administering to the mammal, including humans, a composition comprising live bacteria, wherein the bacteria have been modified to prevent the expression of a functional hydrogenase protein. More particularly, in one embodiment each of the NiFe hydrogenase genes of the wild type pathogen have been mutated to prevent expression of each of the NiFe hydrogenase genes present in the genome of the bacterium. In one embodiment the mutation comprises the deletion of the entire gene, or a portion thereof, of the large and/or small subunit of each hydrogenase gene. In one embodiment the modified bacterium is selected from the group consisting of *Salmonella typhimurium, Salmonella typhi, E. Coli* 0157, *Shigella flexneri, Shigella sonnei*, and *Campylobacter jejuni*. In one embodiment the modified bacterium is selected from the group consisting of *Salmonella typhimurium* and *Salmonella typhi*, and in one embodiment the modified bacterium is *Salmonella typhimurium.*

In accordance with one embodiment, a method of protecting a warm blooded vertebrate species against an infection with pathogenic *Salmonella, E. coli, Shigella*, or *Campylobacter* is provided. The method comprises the step of administering to the subject a live bacterium, selected from the group consisting of *Salmonella, E. coli, Shigella*, and *Campylobacter*, wherein the bacterium has been modified to prevent expression of a functional NiFe hydrogenase protein. In accordance with one embodiment each of the NiFe hydrogenase genes of the wild type pathogen have been modified to prevent expression of a functional NiFe hydrogenase. In one embodiment the modification comprises the deletion of the entire large and/or small subunit of the NiFe hydrogenase genes, or a portion of either or both of those subunit genes.

The compositions can be administered by any of the standard routes known to those skilled in the art. In accordance with one embodiment the live modified bacteria is administered orally at a dose of about $10^4$ to about $10^8$ cfu. In accordance with one embodiment a mammalian species is protected from a *Salmonella* infection by administering a composition comprising a live *Salmonella* strain, wherein each of the NiFe hydrogenase genes present in the genome of the bacterium has been mutated to prevent expression of a functional NiFe hydrogenase protein. In one embodiment a live *Salmonella* strain comprising a triple deletion mutation of each of the three NiFe hydrogenase genes (preventing the expression of a functional NiFe hydrogenase) is administered to mammalian species to decrease the incidence of a *Salmonella* infection that results in diarrheal illness.

The following examples are intended only to further illustrate the invention and are not intended to limit the scope of the subject matter which is defined by the claims.

Example 1

Availability and Use of Molecular Hydrogen as an Energy Substrate for *Helicobacter* Species

*Helicobacter pylori* is a pathogen that solely colonizes the mucosal surfaces of the human stomach, where it gives rise to gastritis, peptic ulcers and is correlated with the development of certain types of gastric cancer. It is a prevalent, but highly treatable infection; the most severe pathologies associated with infection are correlated with both the persistent nature of the bacterium and the highly inflammatory response of the host. *Helicobacter hepaticus* is an enterohepatic type of *Helicobacter* that is receiving research attention due to its association with liver disease (including even liver tumors) in mice. The recent findings of an association of hepatic *Helicobacters* with diseased liver tissue in primates, and the correlations of *Helicobacter*-specific DNA with human patients having primary liver carcinomas has sparked more interest in hepatic *Helicobacter.*

Initially, *H. pylori* grown in the lab with $H_2$ was observed to express a membrane bound "uptake-type" hydrogenase. Reduction of the membrane fraction (the fraction that contained the bulk of the hydrogenase activity) by $H_2$ resulted in the membrane-associated cytochromes acquiring a reduced (ferrous) state, indicating an energy-conserving respiratory chain is operating with the electrons generated from $H_2$. Similarly, the characterizations of the *Helicobacter hepaticus* hydrogenase indicated it is coupled to $H_2/O_2$ respiration as well, but with a significantly lower (whole cell) activity than for H. pylori. Both of the *Helicobacter* spp. hydrogenases are able to couple $H_2$ oxidation with reduction of a variety of positive redox potential acceptors, like other uptake type hydrogenases. No $H_2$ evolution activity could be detected, even when low redox potential reduced dyes were supplied to the cell membranes. Also, like other characterized respiratory hydrogenases, both of the *Helicobacter* enzymes underwent reductive activation, in which highest enzyme activities are observed when the enzyme is reduced.

Hydrogen Availability and Use in Tissues Colonized by *Helicobacter*

The levels of hydrogen gas within the intestinal tracts (primarily the hindgut) of terrestrial arthropods have been relatively well studied in order to understand microbial communities associated with digestion. However, $H_2$ levels in tissues of vertebrate animal hosts had not been assessed until the importance of the substrate to *Helicobacter pylori* infection were ascertained. To study the possible importance of $H_2$ use within animal tissues, $H_2$ levels were assayed in live mice. Both the mucous lining of the stomach as well as the lobes of the liver contained ample amounts of molecular $H_2$, certainly higher levels than were anticipated. The average hydrogen content of the mucus layer of the mouse stomach was determined to be 43 μM (range of 17 to 93 μM), averaging over 20-fold that of the whole cell Km for hydrogen. Similarly, the $H_2$ levels in liver tissue were 20-fold higher than the *H. hepaticus* Km for $H_2$. These measurements in the animal were taken by use of $H_2$ micro electrode inserted into live mice, and it was proposed that these $H_2$ levels were achieved by a combination of cross-epithelial diffusion of the gas from the bowel, and from $H_2$ carried in the bloodstream. By combining the tissue $H_2$ measurements with studies on the binding affinity of the bacteria for $H_2$ (conducted under limiting substrate conditions) it was concluded that *Helicobacter* hydrogenase is saturated with $H_2$ in the host tissues.

A mutant *H. pylori* strain unable to oxidize hydrogen is severely impaired in its ability to colonize mice. A total of 9 mice out of 38 inoculated with the mutant strain contained any detectable *Helicobacter* in their stomach, whereas the parent strain colonized every inoculated mouse. Moreover, for those scored as colonization positive by the mutant the colonization numbers (colony forming units per g of stomach) were markedly less for the mutant than the parent strain. These results indicate that $H_2$ is a major, although not the sole, utilizable energy substrate used by *H. pylori*. The results are convincing that $H_2$ use by *H. pylori* is an important maintenance factor for its survival in the host.

Regulation of Hydrogenase

One characteristic of the bacteria capable of expressing energy-conserving uptake hydrogenases is their ability to sense and then respond (by altering hydrogenase gene expression) to exogenously supplied hydrogen. Hydrogenase activity in *H. pylori* was constitutive under all conditions tested (in rich media), but in a chemically defined media, the activity increased 4-fold when the cells were supplemented with 10% $H_2$. Promoter fusions with a reporter gene were used to address this regulation at the transcriptional level; a 6-fold increase in transcriptional response was observed by the $H_2$ exposure. The enzyme expression response to molecular hydrogen availability is in line with the conclusion that hydrogenase of *Helicobacter* functions in respiratory hydrogen oxidation.

Outlook and Perspective

Hydrogen use is expected to play an important role in setting up the stable infections required for the most serious of the diseases associated with *H. pylori* infection. Colonization and persistence occurs within the complex and viscous mixture of glycoproteins known as mucin. According to physiological studies as well as from the complete genome sequence information, *H. pylori* appears to be limited in its use of oxidizable carbon substrates, and the primary environment for *H. pylori* is also expected to be nutrient poor in regards energy sources available for growth and maintenance. Molecular hydrogen use would thus seem to circumvent some of the colonization barriers faced by *H. pylori.*

Due to the above considerations, it would be expected that (increased) *H. pylori* infection might be correlated with ($H_2$ producing) diet regimes. The proportion of exhaled gas as $H_2$ can vary considerably among individuals so it may be possible someday to correlate *H. pylori* infection with inherent host $H_2$-production characteristics. The prevalence of *H. pylori* infection is thought to depend in part on environmental factors, including diet, age of the individual, or the genetic make-up of the individual or population. Considering the high affinities of the oxidizing hydrogenases for their substrate, $H_2$ levels would have to be reduced within the individual to sub-μM levels, and our data (for mice) indicates levels in tissues are in the 40-60 μM range. Therefore, the microbial fermentations by the colonic flora would have to be dramatically reduced by diet in order to starve a pathogen of (hydrogen) energy. Reducing or eliminating such flora is unwise as such bacteria of course have beneficial attributes for animal nutrition and digestion.

A better approach to reduce $H_2$ consumption by pathogens may be to design inhibitors of the $H_2$ utilizing hydrogenases. These enzymes are oftentimes periplasmic in location and the enzyme contains a highly unique active center containing Ni and Fe with attached CN and CO ligands. Therefore few host would be expected to be adversely impacted by the by use of NiFe active site specific inhibitors. Another approach could be to starve the pathogen of nickel, an essential element for the uptake-type hydrogenases (and for another virulence component, urease).

Other Hydrogen-Utilizing Pathogens

That hydrogen present in animals (as a consequence of normal colonic flora metabolism) is an energy yielding substrate for maintenance of a pathogenic bacterium may be extended to a number of (mostly enteric) pathogens. Based on publicly available complete genome sequence annotations (such as the Institute for Genomic Research, the Sanger Institute, or the National Center for Biotechnology Information) a number of human pathogens have genes encoding all the components required for gleaning energy from $H_2$ respiration. This would include the structural genes for a membrane bound hydrogenase and for shuttling of those electronics to quinone-binding or heme b binding proteins, as well as the accessory proteins for the NiFe hydrogenase enzymes' maturation. These bacteria include *Salmonella* entericaserovars *Typhi* and *Typhimurium, E. Coli* 0157, *Shigella* (*flexneri* and *sonnei*) and *Campylobacter jejuni*. For some of the enterics, H2 oxidation via hydrogenases has been measured (albeit anaerobically).

Most of these pathogens live in the gastrointestinal tract, or within organs that would have ample blood supply (that presumably contains $H_2$). Most of the above bacteria also contain the complete respiratory electron transport chain (normally used in common by $H_2$ and other low potential electrons donors), including one or more $O_2$-binding terminal oxidases. If these bacteria are able to couple $H_2$ oxidation to $O_2$ uptake, it would be expected they could all gain considerable maintenance advantage in colonizing the host.

Example 2

Hydrogenase Deficient *Samonella* Strains and Measurement of Their Virulence Methods and Procedures Based on available annotated gene sequence information the enteric pathogen *Salmonella*, like other enteric bacteria, contains three putative membrane-associate $H_2$ using hydrogenase enzymes. These enzymes split molecular $H_2$, releasing low potential electrons that are used to reduce (quinone or heme-containing) components of the respiratory chain. Here we show that each of the three distinct membrane associated hydrogenases of *Salmonella* enterica serovar *Typhimurium* are coupled to a respiratory pathway using oxygen as the terminal electron acceptor. Cells grown in a blood-based medium expressed 4 times the amount of hydrogenase ($H_2$ oxidation) activity than did cells grown on Luria Broth medium. Cells suspended in phosphate buffered saline consumed two moles of $H_2$ per mole of $O_2$ used in the $H_2O_2$ respiratory pathway, and the activity was inhibited by the respiration inhibitor cyanide. Molecular hydrogen levels are averaging over 40 microM were measured in organs (i.e. liver and spleen) of live mice, and levels within the intestinal tract (the presumed origin of the gas), were 4 times greater than this. The half-saturation affinity of *Salmonella typhimurium* for $H_2$ is only 2.1 microM, so it is expected that ($H_2$-utilizing) hydrogenase enzymes are saturated with the reducing substrate in vivo. All 3 hydrogenase enzymes contribute to virulence of the bacterium in a typhoid fever-mouse model, based on results from mutant strains in each of the 3 genes. The introduced mutations are non-polar, and growth of the mutant strains was like that of the parent strain. The combined removal of all 3 hydrogenases resulted in a strain that is avirulent and (in contrast to the parent strain) one that is unable to invade liver or spleen tissue. Introduction of one of the hydrogenase genes into the triple mutant strain on a low copy number plasmid resulted in a strain that was both able to oxidize H2 oxidation and able to cause morbidity in mice within 11 days of inoculation; therefore the avirulent phenotype of the triple mutant is not due to an unknown spurious mutation. We conclude H2 utilization in a respiratory fashion is required for energy production to permit *Salmonella* growth and subsequence virulence during infection.

It has been suggested that enteric bacteria using hydrogenase enzymes might glean energy from the splitting of molecular hydrogen. This high-energy gas is produced by colonic flora within animals. Because $H_2$ is freely diffusible, the gas can be measured within both intestinal and non-intestinal tissue (see Maier, et al., (2003) J. Bacterial. 185: 2680-2682). As described herein, $H_2$ utilization plays an important role in the pathogenicity of *Salmonella typhimurium*, a common food poisoning bacterium closely related to the typhoid fever-causing bacterium *S. typhi*. More particularly, the role of enteric $H_2$ use was assessed in the mouse model of typhoid fever.

Mutant strains at STM numbers (for the large subunit) 3147, 1538, and 1787 were generated; these correspond to gene designations hybC for S™3147, and hydB for the other two sites. Also, the hydrogenases of *S. typhimurium* were determined to function in a respiratory ($H_2$-oxidizing) fashion by a mutant analysis approach.

Materials and Methods

Amperometric Hydrogenase Assays.

The conditions for obtaining hydrogenase activity involved growing cells on a blood-containing medium (Olczak, et al., (2002) J. Bacteriol. 184:3186-3193), in a microaerobic $H_2$ containing atmosphere (see Table 1 legend). *S. Typhimurium* cells grown one day on the BA plates were suspended in a phosphate-buffered saline, and 8 ml samples at cell concentrations of $8\times10^8$ cells per ml were assayed for $H_2$ and $O_2$ uptake activities simultaneously. This was accomplished on the same sample in a stirred and sealed amperometric dual-electrode chamber (Merberg, et al., (1986) Bacteriol. 156:1236-1242). Hydrogen and oxygen were added as needed from gas-saturated solution of phosphate buffered saline. H2 uptake rates were linear until the substrate reached levels of about 3 to about 5 μM. For methylene blue dependent rates, the chamber lacked oxygen but contained MB at 200 μM, and the cells were permeabilized with TRITONX-100 before assay. Cell numbers were determined by performing dilutions and plate counts on MacConkey medium. For determining affinity of whole cells for $H_2$, the $H_2/O_2$ uptake assay was performed in a series of limiting $H_2$ levels between 1.2 and 10 μM. The $O_2$ level was saturating for all these assays, but was maintained below 55 μM, as the affect of high $O_2$ levels on the three separate (hydrogenase) enzymes is not known. The double reciprocal plot yields a line equation, for which kinetic parameters can be calculated. The Km from this data is referred to herein as the half saturation affinity for $H_2$, because in our case the kinetic constants are for a whole cell system rather than for the pure enzyme (the latter being the conventional system for such determination).

Mutant Strain Construction.

All mutations were in the structural genes for hydrogenase and were constructed in a way so as not to disrupt downstream genes. The three hydrogenase genes targeted are ones that are homologous to genes encoding membrane-associated NiFe uptake hydrogenases (a fourth putative hydrogenase in *S. typhimurium* is homologous to the hydrogenase termed HycE of *E. coli* that is proposed to be associated with electron transfer reactions within a formate hydrogen lyase complex. Although the 3 targeted enzymes are predicted to be membrane-bound NiFe types, and were homologous to the *E. coli* hydrogenases, assigning them to genes using the *E. coli* nomenclature (like hya genes) was not possible due to strong cross-homologies. Therefore these three genes are referred to herein as gene Groups I, II, and III, and the specific gene numbers disrupted are described.

*S. typhimurium* strain ATCC14028 (JSG210) was used as the parent for the construction of all the mutants. The Lambda Red system was used to construct deletion mutations in the hydrogenase genes (Datsenko, et al., (2000) Proc Natl Acad Sci. USA, 97:6640-6645). The nucleic acid sequence of these genes can be found in the NCBI nucleotide database at accession numbers AE008844, AE008766 and AE008779, respectively (see also McClelland, et al., Nature (2001) 413: 852-856).

A schematic overview of the steps used to create the hydrogenase deletions is provided in FIG. 1. Briefly, an antibiotic cassette located on plasmid pKD4 was amplified by PCR. Primers were designed (at their 5' ends) to contain homologous sequences to the DNA outside the fragment assigned for deletion. Primers were designed to delete a 4972 bp region of Group I genes (STM 3147 through STM 3150) represented by coordinates 3313762 to 3308790 in the TIGR comprehensive microbial resource for *S. typhimurium*. Group II gene deletion included genes STM 1538 and STM 1539 by creating a 2905 bp deletion fragment (coordinates 1614904 to 1611999 deleted). For Group III, a deletion of 2905 bp was made (coordinates 1884828 to 1887733 which includes genes STM 1786 and STM 1787). Genes within the deleted regions encoded hydrogenase large and small subunits.

More particularly, the following PCR primers were used to create the deletion mutations in the respective Group I, II and III *S. typhimurium* hydrogenase genes.

```
Hydrogenase mutant I:
                                         (SEQ ID NO: 1)
JG620 5' TAG TGG TTT GGG ATA AAC GTT ATG CAA ACA

GTG TAG GCT GGA GCT GCT TCG 3'
Deletion Primer upstream of STM3147 for deletion
of STM3147-STM3150 (Used with JG 621)

                                         (SEQ ID NO: 2)
JG621 5' ATT GAG ACC TCC GAA TCG TCG TCA TCG TAC

CAT ATG AAT ATC CTC CTT AG 3'
Deletion Primer upstream of STM3150 for deletion
of STM3147-STM3150 (Used with JG620)

Hydrogenase Mutant II:
                                         (SEQ ID NO: 3)
JG624 5' TCG TAA CGG AAT AAC TAT AAA ATG TGT GCA

GTG TAG GCT GGA GCT GCT TCG 3'
Deletion Primer downstream of STM1538 for deletion
of STM1538-STM1539 (Used with JG625)

                                         (SEQ ID NO: 4)
JG625 5' CCC CTA AGA CTA ATA TCC GCA TTA CAA AAC

CAT ATG AAT ATC CTC CTT AG 3'
Deletion Primer upstream of STM11539 for deletion
of STM1538-STM1539 (Used with JG624)

Hydrogenase mutant III:
                                         (SEQ ID NO: 5)
JG628 5' AAA GGA GAA AAA ATA CGC GTT ATG AAT AAC

GTG TAG GCT GGA GCT GCT TCG 3'
Deletion Primer upstream of STM1786 for deletion
of STM1786-STM1787 (Used with JG629)
```

-continued (SEQ ID NO: 6)
JG629 5' ATC GTT CTT TTC CTT AAC GCT TAG CGT ACC

CAT ATG AAT ATC CTC CTT AG 3'
Deletion primer downstream of STM1787 (used with JG628)

Each of the PCR fragments was transfected by electroporation into a strain of *Salmonella typhimurium* containing the Red helper plasmid (a temperature sensitive plasmid encoding enzymes that prevent degradation of incoming linear DNA) allowing uptake of linear DNA and recombination. After selecting for the transformants comprising the appropriate insertion, the antibiotic resistance cassette in the mutants was eliminated by transforming the strains with the FLP synthesis inducing plasmid, pCP20 (Datsenko, et al., (2000) Proc Natl Acad Sci. USA, 97:6640-6645). FRT-flanked resistance genes, as well as FLP helper temperature sensitive plasmid, were both lost at 43° C. Double mutants were obtained by P22 HTint-mediated transduction of an antibiotic marked single gene deletion strain into the appropriate single gene deletion strain by antibiotic selection, followed by transformation with the pCP20 plasmid and elimination of the antibiotic cassette. The triple mutant was constructed in a similar manner using the appropriate double deletion mutant (genes I and II negative) as the recipient.

The deletion endpoints are demonstrated below for each of the three groups of genes. Approximately 100 bp both upstream and downstream of the hydrogenase deletion sites is shown. Group I represents the deletion of genes STM 3150-3147), Group II represents the deletion of genes STM1539-1538), and Group III represents the deletion of genes STM1786-1787). The site of the deletion is indicated in each sequence.

Group I
(SEQ ID NO: 7)
GCGTCGGCAATGATCAAATGATCACGATTCGCCATATCGCCAAGAAGTTC

CATTCCCGCCACAATACGCACCCCGATGGCTTCATCGGTCAGCAAAATAT

TGCCGACCCCTAAGACTAATATCCGCATTACAAAAC (deletion site)

TGCACAAAGCTTCATGAAATCACGACGGTTAATGCCGTGAGAAGTGATGA

GAGTATTATCTCCAGTCATTTTATAGTTATTCCGTTACGAAGACCT.

Group II
(SEQ ID NO: 8)
GTACTCATTGCCGACACATGCCCAGTAAATACGAAACAGCAGCGCGACAG

TAAAAATATACGCCGTGGTAAAATGGATCAGTCGTATCCAGCCCATCCAA

AACATAAAGGTCGCTTCACCTTGAATCGATGGCAGGGGGCGGCCAATGAA

ATATCCTGTAACAGCCAGGACGACAATGGATAACGCCGTGATCCAGTGCC

ATAAACGGACCGGCGCTTCATAGATATAGTACCCCTGGCTGGTTATTTCT

TTGAGATGCATTGAGACCTCCGAATCGTCGTCATCGTAC (deletion site)

TGTTTGCATAACGTTTATCCCAAACCACTATAGTTAGTGTGGGCATCATA

TGTTGCATTTCTTGTCTTTCTCAACGTGTTTTAGTAGCAATTATGTTTCT

AATTCGTAACAACTGATTACATGTGTGCTACTCACATTACTCAAAAACAT

-continued

AAATTAATTTAATGTTATTGGTGATGTTGAGTAAATATAGCGTTGTGATG

GCATCTCTTAATGTTGATAAGAAACCGTG.

Group III
(SEQ ID NO: 9)
CTTATCGTTAATCCGATACGCTTTTTTCACATTATTTCTGGCGGTATACG

CCGGTGCAAAGTGAATCGGGCTCGTTTCCGCGCTCGCGCGTAACACAATG

ATTTACCTTGCTGGCGGAACGTCAACGGACCCGCAAAAGCGCCTTATGCC

CCTGGCGGAGCGTGGTGCAAAAAGGAGAAAAAATACGCGTTATGAATAAC (deletion site)

GGTACGCTAAGCGTTAAGGAAAAGAACGATGACTGGAAAGCTATCTCCAC

GCGTCGGGGAGGCGCGTGATACTGCCGTCAGCCACTATGTGTTTGAAGCG

CCGGTACGCCTGTGGCACTGGCTAACGGTGGCC.

All deletions were confirmed by PCR with primers designed outside of the deleted-DNA regions. For the Group I gene, primer JG622 (5'CAC GGT TTC TTA TCA ACA T 3'; SEQ ID NO: 10) was used as the Checking Primer downstream of STM3147, and primer JG623 (5' GTA CTC ATT GCC GAC ACA TG 3'; SEQ ID NO: 11) was used as the Checking Primer upstream of STM3150. For the Group II gene, primer JG626 (5'CCG GGA TGG CGG TTC GCT TC 3'; SEQ ID NO: 12) was used as the Checking Primer downstream of STM1538 and primer JG627 (5' GCG TCG GCA ATG ATC AAA TG 3'; SEQ ID NO: 13) was used as the Checking Primer upstream of STM1539. For the Group III gene primer JG630 (5'CTT ATC GTT AAT CCG ATA CGC 3'; SEQ ID NO: 14) was used as the Checking Primer upstream of STM1786 for deletion of STM1786-STM1787 and primer JG631 (5' GGC CAC CGT TAG CCA GTG CC 3'; SEQ ID NO: 15) was used as the Checking Primer upstream of STM1786 for deletion of STM1786-STM1787.

Each deletion left a few base "scar" in place of the deleted DNA. The scar region contains a ribosome-binding site at the 5' end as well as a start codon, which will allow reengagement of the ribosome for the downstream gene transcription. Also, rtPCR of genes directly downstream of the deletion (for Group I, STM 3145, for Group II, STM1536, and for Group III, STM1789) was performed in order to confirm the lack of polar affects. Additionally, expression of STM 3142 (ferrichrome-binding periplasmic protein) was measured by rtPCR in the triple mutant strain and was found to be the same as for the wild-type strain. Therefore, the expression of genes downstream of the deleted regions was unaffected, so the results presented are due to hydrogenase deficiencies only. Strain numbers corresponding to the introduced double deletions and the triple mutant are given in the FIG. 2 legend, and two other strains (containing a low copy plasmid) are described in the following paragraph.

Primers JG915 (5'GCTCTAGAAAAAATACGCGTTATG 3'; SEQ ID NO: 16) and JG916 (5'CCCAAGCTTAGCGTACCTGGACGGC 3'; SEQ ID NO: 17) were used to generate a PCR product containing STMI786 and STM1787. These two genes correspond to those missing in the Group III deletion strain. The PCR fragment was cloned into p WSK29 (Wang et al., (1991) Gene 100:195-9) using the XbaI and HindIII sites engineered into the 5' ends of JG915 and JG916, respectively. STM1786 and STM1787 are expressed from the lac promoter of the vector. The resultant plasmid pG3229 was transformed by electroporation into strain JSG321, the triple hydrogenase gene mutant, creating strain JSG2495. The plasmid vector pWSK29 was also transformed into strain JSG321, creating JSG2497.

Mouse Experiments

BALB/c female mice (obtained from the National Cancer Inst at Frederick Md.) were inoculated orally as described previously (Tamayo, et al., (2002) Infect. Immun. 70:6770-6678) with 0.1 ml amounts of washed cells (containing $1\times10^6$ bacteria) suspended in PBS. Mice were observed twice daily and morbidity recorded. The organ burdens of bacteria post-inoculation were obtained by euthanizing mice (96 hr after inoculation of four mice with each bacterial strain). The liver and spleen were immediately removed from the euthanized mice, and the organs were homogenized (in PBS). Dilutions were plated onto MacConkey agar, a medium selective for Gram-negative lactose-negative bacteria, and colonies were counted the next day. No colonies were observed from homogenized organs from (two mice in the same cage) uninoculated mice.

Measurements of $H_2$ levels within the small intestine of mice were performed by making a small incision into the intestinal wall with a razor blade, and inserting a 50 μmeter tip size $H_2$ microelectrode probe less than 0.5 mm into the intestine. For splenic $H_2$ determinations, the probe was placed from 0.2 to less than 1.0 mm into the spleen tissue as described previously for $H_2$ measurements in liver tissues of live mice. These determinations (including instrument calibrations) were performed like those described in detail previously for $H_2$ measurements in other tissues (Maier, et al., (2003) J. Bacterial. 185:2680-2682). Care was taken to keep all the organs as intact as possible during surgery and for microelectrode measurements, and the mouse was kept under anesthetic for the procedure. Acquiring a stable $H_2$ signal within the tissue sometimes required no probe movement for up to 12 sec. Twelve independent measurements were made (four each on 3 separate mice) for each tissue and the mean of these is reported.

Results and Discussion

Characteristics of $H_2$ Oxidation Activity.

*Salmonella typhimurium* hydrogenase activity has been previously ascribed to at least two distinct but similar membrane associated hydrogenases, and possible roles for these enzymes in anaerobic energy metabolism were proposed (Bock, A., and G. Sawers, in *Escherichia coli* and *Salmonella typhimurium*, Chap. 18, see. (ASM Press, Washington, D.C 2002), F. C. Neidhardt). The complete genome sequence of *S. typhimurium* LT2 indicates the bacterium contains genes for three putative homologous membrane-associated H2 utilizing type hydrogenases (Institute for Genomic Research; TIGR). Although previously-reported *S. typhimurium* hydrogenase activity was always been performed anaerobically, the gene annotated sequence reveals that *S. typhimurium* has several $O_2$ binding oxidases that could perhaps allow for the complete respiratory oxidation of electrons from $H_2$ all the way to $O_2$ reduction. If the reductant $H_2$ could be used simultaneously with $O_2$ as the acceptor (i.e. via respiration), then it is expected that a high efficiency energy yield would be available to allow $H_2$ mediated growth of cells. This is a common role for NiFe hydrogenases in many aerobic bacteria.

Accordingly the $H_2$ oxidation coupled to $O_2$ dependent respiration was measured in the parent strain in various gas atmospheres and culture medium conditions, including Blood agar and micro aerobic atmospheres (See Table 1). Previous enteric bacteria hydrogenase studies used cells grown on either a glucose-peptone medium (Sawers, et al., (1986) J. Bacteriol. 168:398-404) or on LB medium (Jamieson, et al., (1986) J. Bacteriol. 168:405-411) under strictly anaerobic conditions. $H_2$ oxidation was monitored herein simultaneously with ($O_2$-dependent) respiration by use of $H_2$ and $O_2$ electrodes on the same (sealed and continuously-stirring) samples.

TABLE 1

Variations of Growth Conditions for Obtaining Respiratory $H_2$ Oxidizing Activity

| Condition | Description | | Activity (nmoles $H_2$/min/ |
|---|---|---|---|
| No. | Medium | Gas atmosphere | $10^9$ cells) |
| 1 | Blood Agar | Anaerobic Mix | 11.9 ± 1.5 |
| 2 | Blood Agar | Anaerobic Mix, but 2% $O_2$ | 3.2 ± 0.4 |
| 3 | Blood Agar | CAMPYPAK system | 2.1 ± 0.3 |
| 4 | Blood Agar | Anaerobic Mix, but 8% $O_2$ | <0.2 |
| 5 | Blood Agar | Anaerobic Mix, but without $H_2$ | 7.2 ± 1.2 |
| 6 | Luria Bertani Agar | Anaerobic Mix | 2.8 ± 0.4 |
| 7 | Luria Bertani Agar | Anaerobic Mix, but 2% $O_2$ | <0.2 |
| 8 | Luria Bertani Agar | CAMPYPAK system | 1.2 ± 0.1 |
| 9 | Luria Bertani Agar | Anaerobic Mix, but 8% $O_2$ | <0.2 |
| 10 | Luria Bertani Agar | Anaerobic Mix, but no $H_2$ | 1.3 ± 0.3 |

* Anaerobic mix consists of 10% $H_2$, 5% $CO_2$, balance $N_2$. After sparging with this mixture, $O_2$ levels were below 0.2% partial pressure, but were not anaerobic. Results are mean ± std. dev. For 5 replicate independent samples. BA = Blood Agar LB = Luria Broth CAMPYPAK is a $H_2$ and $CO_2$ generating system that depletes $O_2$; initially the atmosphere is air, but less than atmospheric $O_2$ is achieved.

In addition to Luria Broth, Blood Agar was tested as a possible high nutrient growth medium to enable hydrogenase expression. This proved to be highly beneficial to hydrogenase expression (Table 1). The parent strain was able to readily oxidize $H_2$ at rates observed for another $H_2$ oxidizing pathogenic bacterium (*Helicobacter pylori*) under the same incubation conditions (i.e. Blood agar plus a microaerobic $H_2$ containing atmosphere). Salmonella activities on Blood Agar were 4 times that on Luria Broth when both were incubated with anaerobic gas mix (Table 1, compare no. 1 with no. 6). Oxygen repressed hydrogenase expression, as seen by comparing conditions 2 or 4 with no. 1 (also compare condition 7 or 9 with no. 6). This $O_2$ repression phenomenon on hydrogenase expression is common for respiratory hydrogenases. Also, incubation with $H_2$ augmented expression, as seen by comparing condition no. 1 with 5, and no. 6 with no. 10.

Additional Characteristics of $H_2$ Oxidation.

Figure 2:
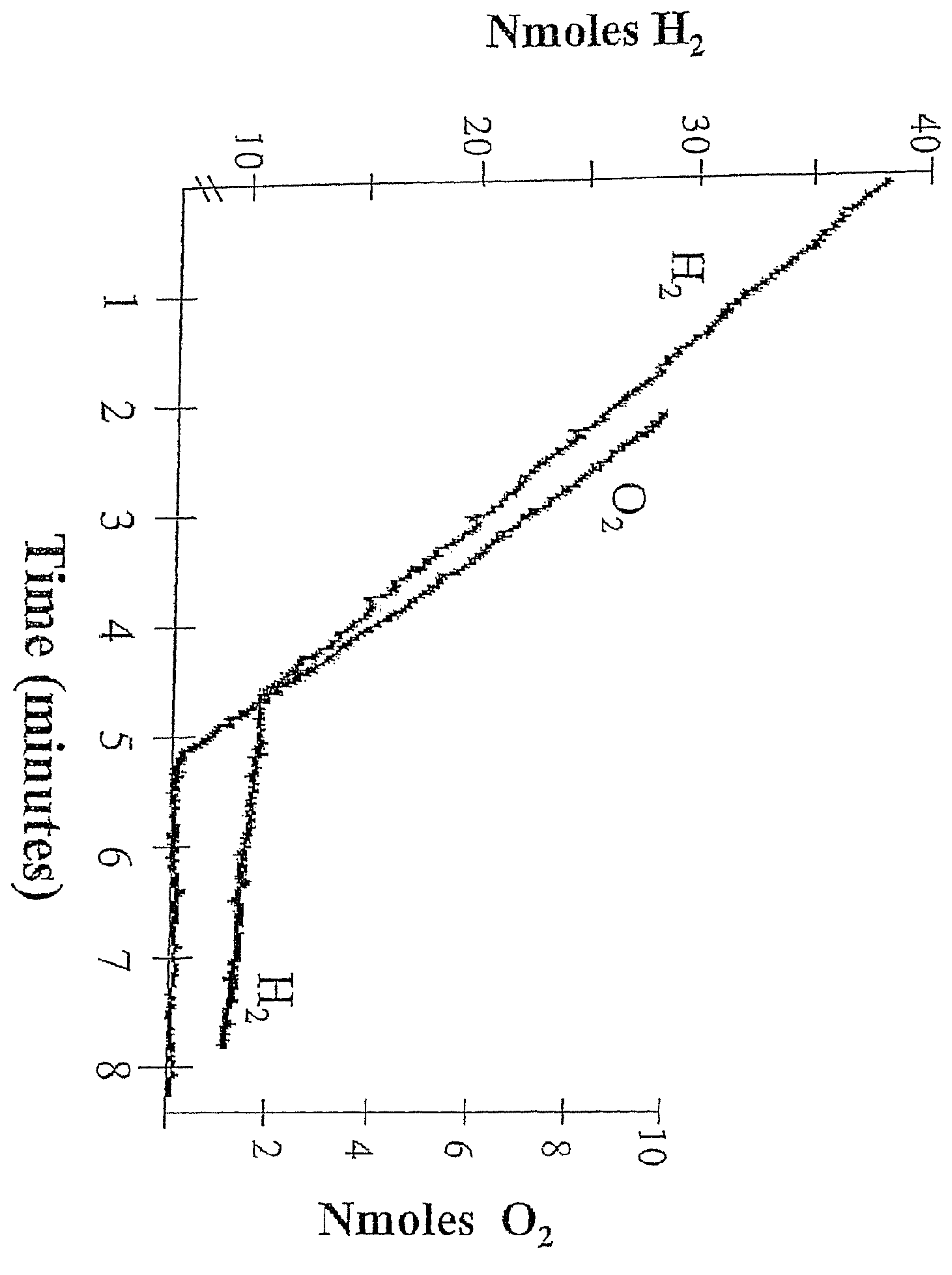
FIG. 2 is a graphic representation of the dual channel amperometric recording of simultaneous $H_2$ and $O_2$ use by whole cells of *Salmonella typhimurium*. $H_2$ and $O_2$ were injected into the (5.5 ml vol.) amperometric chamber from gas-saturated solutions and the gases were monitored continuously by amplified amperometric electrodes signals on a chart recorder. The chamber contained $6.8\times10^8$ washed *Salmonella typhimurium* (wild type) cells obtained from blood agar plates. The cells were suspended in PBS, and the assay conducted in PBS. Oxygen is exhausted at about the 5 min time period, and the minimum detectable level is about 20 nM. The $O_2$ pen is offset in the figure to record approximately 30 seconds ahead of the $H_2$ pen.

A direct amperometric recording of whole cells of *S. typhimurium* using both $H_2$ and $O_2$ as dissolved gases in the buffer is shown in FIG. 2. Nevertheless, some $H_2$ oxidation occurred after $O_2$ was exhausted (FIG. 2). As seen, when $O_2$ is exhausted (at about the 5 min mark in FIG. 2), $H_2$ uptake slows, but continues at a slow rate (approximately 8% of the aerobic rate, and this diminished rate is maintained for about 7 to about 10 min). After this diminished activity, over the next 3-4 min time period, $H_2$ uptake diminishes more and ceases entirely. This was observed in over 10 different assays, and was never observed when assaying other $H_2$ oxidizing pathogenic bacteria, such as for *Helicobacter pylori* or *H. hepaticus* (Maier, et al., (2003) J. Bacterial. 185:2680-2682.). The "anaerobic" $H_2$ oxidation was attributed to endogenous acceptors perhaps organic acids like fumarate) still present within the bacterium, or perhaps to residual electron acceptors present in the medium. These predictions are supported by the observation that incubation of cell suspensions (cells removed from the blood agar medium into PBS) incubated in an $H_2$-containing atmosphere for 10-30 min at room temperature resulted in cells that no longer exhibited the anaerobic $H_2$ respiration activity (i.e. terminal substrate is presumably exhausted). Normally cells were suspended in PBS and assayed immediately, so a low rate of $H_2$ oxidation occurred without $O_2$. By performing hydrogenase assays in the absence of oxygen, along with use of mutant strains (see below) some, but not all, of the endogenous or anaerobic activity (which is the minor $H_2$ respiration activity) could be assigned to function of hydrogenase of gene Group I, but hydrogenase number I is also responsible for $O_2$ dependent $H_2$ oxidation/respiration (Table 1).

In FIG. 2, it can also be observed that the stoichiometry of $H_2/O_2$ respiration for washed cells in PBS is approximately 2 moles of $H_2$ oxidized per one mole of $O_2$ consumed. After the anaerobic $H_2$ oxidation rate ceased, and $O_2$ was supplied again, the stoichiometry of $H_2$ uptake to $O_2$ uptake was measured more precisely at 2.0, as expected for the complete oxidation of $H_2$ by $O_2$. That the bulk of $H_2$ oxidation (even in the first 5 min of the assay) occurs via respiration to $O_2$ was corroborated by cyanide inhibition experiments as follows. Addition of 0.1 mM cyanide to the *S. typhimurium* cell suspension prior to the start of the $H_2$ uptake assay (15 min incubation with sodium cyanide in an argon-sparged atmosphere) inhibited 52% of the hydrogenase activity compared to the no inhibitor activity, and addition of 1.0 mM cyanide inhibited 90% (to 10% of the no inhibitor added) of the $H_2$ uptake activity. The cyanide additions did not affect the methylene blue dependent $H_2$ uptake activity (i.e. the $H_2$ splitting hydrogenase reaction), so the inhibitor must be acting at the level of the $O_2$ binding heme-containing proteins (as expected).

Hydrogenases that consume molecular $H_2$ typically have high affinities for the substrate. By performing $H_2$ uptake assays amperometrically (with $O_2$ as the terminal acceptor) including in limiting $H_2$ levels the half saturation affinity for $H_2$ by wild type *S. typhimurium* was determined to be 2.1 μM. This was determined from the activities of whole cells at nine separate $H_2$ concentrations and from a linear transformation of the data in the form of a double reciprocal plot yielding a line equation y=bx+a, where b and a are 1.1475 and 0.5545, respectively.

Mutant Strain Characterizations.

Mutant strains in the NiFe hydrogenases were made at STM3147, STM1538, and STM 1786. The mutations are referred to as hydrogenase gene Groups I, II, and III respectively. Table 2 provides the STM numbers for the disrupted large subunit of hydrogenase for the various mutants, the TIGR-assigned gene designation for each hydrogenase, and our measured $O_2$-dependent $H_2$ oxidation activities of the wild type and mutant strains. Individual single mutant strains in each of the 3 hydrogenases all had decreased $O_2$ dependent $H_2$ uptake activity compared to the parent strain (Table 2); this indicates that each of the 3 enzymes contribute to respiratory $H_2$ oxidation. Still, one of the three enzymes (encoded in gene Group I, and designated hybC) is a lesser contributor to the overall activity (in laboratory conditions) compared to the other two hydrogenases. All double mutant combinations showed further reduced activity compared to the parent or the single mutant strains. Only the mutant strain lacking all 3 hydrogenases failed to oxidize $H_2$. The growth rate in LB liquid medium was the same for wild type and the triple mutant.

TABLE 2

Aerobic $H_2$ Oxidation Activity by *S. typhimurium* Strains

| Strain | Nmoles/min/$10^9$ cells |
|---|---|
| wild type | 13.3 ± 1.1 |
| $H_2$ase I mutant (STM 31.47, hybC) | 10.6 ± 0.6 |
| $H_2$ase II mutant (STM 1538, hybB) | 5.2 ± 0.8 |
| $H_2$ase III mutant (STM 1787, hybB) | 8.1 ± 0.7 |
| $H_2$ase $I^-$ $II^-$ mutant | 2.0 ± 0.3 |
| $H_2$ase $I^-$ $III^-$ mutant | 3.1 ± 0.4 |
| $H_2$ase $II^-$ $III^-$ mutant | 0.8 ± 0.2 |
| Triple $H_2$ase mutant | <.20 |

Virulence

Figure 3:
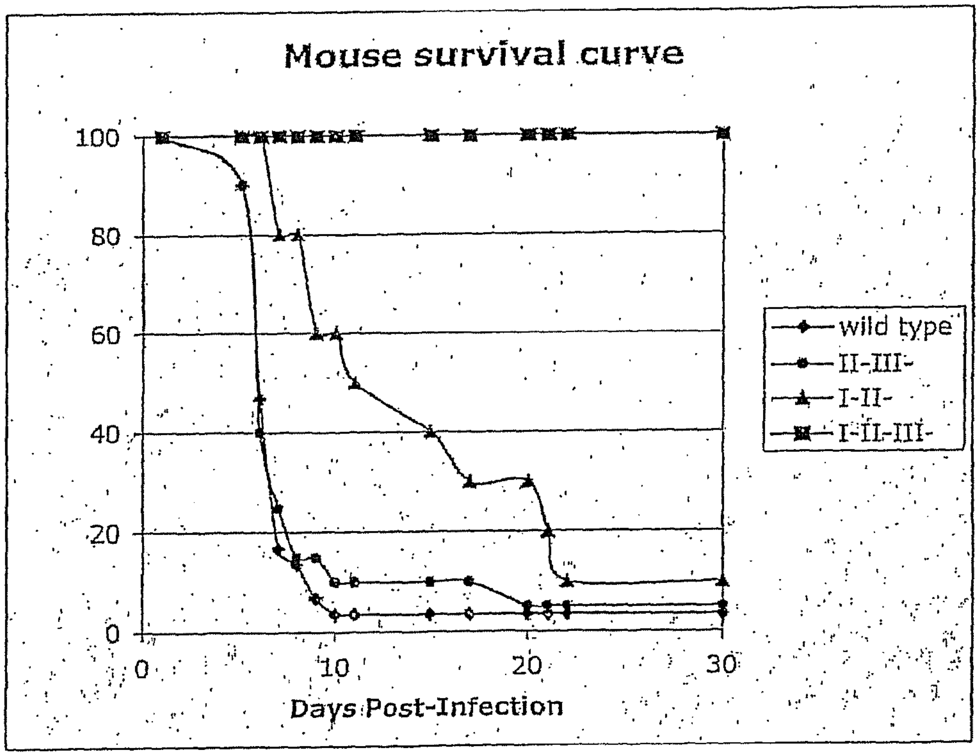
FIG. 3 is a graphic representation of data generated from testing the virulence of the modified *Salmonella typhimurium* strains on mice. The data shown is from a total of 30 mice each for the wild type and the triple mutant strain, based on the combined data from two separate experiments. The y-axis is the percent survival. The inoculant was $1\times10^6$ cells introduced orally. For JSG319 (Group $II^-III^-$), 20 mice were used, and 10 mice for JSG315 (Group $I^-II^-$). Data for another double mutant strain (JSG317, Group $I^-III^-$) is not shown but was similar to the results obtained for strain JSG 315.

To assess the ability of the strains to cause disease, a common mouse model was used. This assay uses death as the endpoint, as the bacterium is highly invasive in mice, resulting in typhoid fever like symptoms. The results are shown in FIG. 3. As observed in other *S. typhimurium* virulence studies, the wild type strain caused death of most of the mice within 10 days of oral administration. All double mutant strain combinations were either as virulent as the parent strain (see FIG. 3), or (for the strains containing only hydrogenase II or III) somewhat less virulent than the parent. Nevertheless, the presence of any one of the three hydrogenases is sufficient for the bacterium to cause severe disease, as the virulence characteristics of all three double mutant strain combinations showed that all 3 enzymes are individually sufficient for virulence (i.e. at least 50% of inoculated mice were dead at day 11 post-inoculation for all double mutant strains). The strain containing only hydrogenase I retained nearly full virulence, but the importance of hydrogenases II and III are shown by the result that a hydrogenase I mutant had nearly the same virulence capacity as the wild type.

The triple mutant strain JSG321 was clearly less virulent than the parent strain. Indeed out of 30 inoculated mice with that strain, none died. All mice that survived to day 30 were also still alive at day 40. Both the triple mutant (stain JSG321) and the double mutants (the $I^-III^-$ and $I^-III^-$ strains, but not the $II^-III^-$ strain) were significantly less virulent than the parent strain according to the alternative Wilcoxin test, with γ=0.992 (wild type vs. triple mutant) or γ=0.988 (for the wild type vs. double mutants). Still the triple mutant was significantly less virulent than the double mutants, with no morbidity observed by the triple mutant strain over a 40 day post-inoculation period. The expression levels of the 3 hydrogenase enzymes within the animal is not known, but due to the in vivo results it is clear that the hydrogenase of Group I, a minor contributor to the overall lab-grown activity, is an important enzyme for virulence.

Organ Burden, and Hydrogen Levels Measured in Tissues.

Liver and spleen colonization numbers by the triple mutant and the wild type was determined four days post inoculation ($1\times10^6$ cells introduced orally into each of the four mice for each bacterial strain) with the result that viable *S. typhimurium* were recovered from the organs of mice inoculated with the parent ($H_2$-using) strain, but no cells were recovered from mice inoculated with the triple mutant. The range of colonization numbers (*S. typhimurium* recovered 96 hrs after inoculation) among 4 mice inoculated with the wild type was between $5.0\times10^4$ to $1.9\times10^5$ CFU per liver, and $3.0\times10^4$ up to $1.8\times10^5$ CFU per spleen. Therefore it is possible that the mutant strain is eliminated from the intestine or during transit to the mesenteric lymph nodes.

Complementation of the Triple Mutant.

To rule out the possibility that an unknown mutation (unrelated to $H_2$ metabolism) occurred in the triple mutant that severely affects its virulence, one of the 3 hydrogenases was reintroduced into the triple mutant strain. Strain JSG2495 is the triple mutant strain containing the genes corresponding to the Group III deletion on a low copy vector; its $H_2$ oxidation and virulence characteristics were studied in comparison to the triple mutant strain containing the vector alone (strain JSG2497) and to the wild type strain and the Group I and II double mutant strain JSG315 (i.e. the latter contains only hydrogenase corresponding to gene Group III). In an experiment similar to the one used to generate the data presented in Table 2, the $H_2$ oxidation activity of the partially complemented triple mutant strain (JSG2495) was (in mnoles $H_2$/min/$10^8$ cells, mean±std dev of four replicates) 4.1±0.5, and about 2 times that of strain JSG315 (1.9±0.4), and about one-third that of the wild type strain (14.4±2.0). No activity could be detected when four replicate samples of the triple mutant strain containing the vector alone (strain JSG2497) were assayed. The morbidity on mice associated with these strains was determined as described above for the other mutant strains. Out of five mice inoculated with each strain, the number that were still alive at day 17 post-inoculation for each strain (number alive in parentheses) was as follows: wild type (O), JSG2495 (2), strain JSG315 (2), and finally for the mutant strain containing the vector only, strain JSG2497 (5). Two of the three mice that died within 15 days due to inoculation with JSG2495 died within 11 days of the oral administration. Therefore the introduction of one of the hydrogenases into the triple mutant restored significant virulence capacity, to a degree that was similar to the strain that is able to synthesize only Group III hydrogenase.

It has been proposed that $H_2$ produced by colonic bacteria might reach tissues within animals by a combination of cross-epithelial diffusion and vascular-based transport processes. Molecular hydrogen levels ranged from 118 up to 239 μM in the small intestine of live mice (the mean value for 12 determinations was 168 μM), and spleen tissue $H_2$ levels were similar (approximately 43 μM) to that previously reported previously for liver tissue (Maier et al., (2003) J. Bacterial. 185:2680-2682). In either case, these $H_2$ levels are higher than the amount needed to essentially saturate whole cell hydrogenase, based on affinities of the bacteria for $H_2$ when grown in the lab. For intestine and liver/spleen the measured levels were about 80 and 20 fold respectively, above the half saturation value of the cells of about 2 μM. Thus a rapid turnover of the $H_2$ is expected through hydrogenase activity, especially in (intestinal) environments where enteric bacteria can thrive.

The use of $H_2$ in an $O_2$ dependent respiratory pathway by *Salmonella* would be expected to result in ATP production to bolster cell growth. The animal results here demonstrate the importance of $H_2$ use by an enteric bacterium for survival/growth in vivo. It is likely that this is a common mechanism of energy generation by enteric pathogens within the host. The intestinal flora is the presumed source of $H_2$ and the fermentation reactions they carry out would be expected to provide a continuous supply of molecular hydrogen. In addition, the host does not use this high-energy substrate, so that even in conditions when the host is nutrient poor in terms of sugars or peptides in the serum, the pathogen can grow. With the uniformly high affinity for $H_2$ by studied uptake hydrogenases, even in conditions of low $H_2$ in the bloodstream (lower than have been measured herein), the pathogen should readily oxidize the high energy reductant. The advantage to the pathogen is obvious as the host cannot use this substrate.

Some of the pathogenic enteric bacteria can now be considered to use molecular hydrogen as a critical growth substrate in the animal. This adds an important group of bacteria to the range of pathogens (like *H. pylori*) able to use $H_2$ as a growth substrate to colonize the host. *Helicobacter pylori* contains a single $H_2$ utilizing membrane bound hydrogenase, with a high $H_2$ affinity. Another gastrointestinal pathogen that is physiologically similar to *H. pylori* and contains a NiFe $H_2$ uptake hydrogenase is *Campylobacter jejuni*.

The reason for the enteric bacteria having 3 similar (but all active) $H_2$ using enzymes is unknown, but could be related to different environments they encounter. It will therefore be interesting to determine the affinities for $H_2$ of each of the hydrogenases separately, along with determining the tissue specific expression of each $H_2$ utilizing enzyme; it would be expected that the high affinity enzymes would be most useful to the bacterium in the tissues with lowest $H_2$ levels (i.e. liver/spleen) and that the lowest affinity enzymes could function well in abundant $H_2$ levels (i.e. the intestine). *Helicobacter pylori* contains a single $H_2$ utilizing hydrogenase, also with a low half-saturation affinity (1.8 11 M) for the gas, but the bacterium has a very limited colonization range in the host. The identification of agents that selectively inhibit bacterial hydrogenases (with their unique active centers containing Ni, Fe, CN, and CO) may represent potential therapeutic strategies for the elimination of *salmonella*-based and other enteric infections.

Example 3

Use of Hydrogenase Deficient Strains to Protect Against Pathogenic Disease

As the following data demonstrate, use of the triple mutant hydrogenase deficient strains (unable to use molecular hydrogen) as a pre-challenge to a lethal dose of the virulent ($H_2$-oxidizing) strain results in protection of the animal from disease (salmonella-induced typhoid fever). Not a single animal died or showed disease symptoms if it was first inoculated with the mutant strain.

Methods

20 Balb/c female mice were obtained from The Jackson Laboratory, 610 Main Street, Bar Harbor, Me. 04609-1500. On day 1, 20 mice were inoculated with $10^6$ cells of *Salmonella typhimurium*, triple mutant. This mutant had the following deletions:

Group I—(STM 3150, STM 3149, STM 3148, STM 3147); Group II—(STM 1539, STM 1538); and Group III—(STM 1786, STM 1787). All of the mice survived.

Fifty days after inoculation with the *Salmonella typhimurium*, triple mutant, the 20 mice were inoculated with 100 μl containing $5\times10^6$ cells/100 μl of wild type *Salmonella typhimurium* were administered to the mice by oral gavage. Mice were checked daily, and all appeared asymptomatic. The wild type strain (an $H_2$ oxidizing strain) used as the challenge has been previously shown to be lethal. Previous experiments have shown that by day 11 all mice inoculated with this wild type strain at $1\times10^6$ cell dost per animal were dead.

Eleven days after being challenged with wild type *Salmonella typhimurium*, every mouse was symptom free. All 20 mice remained symptom free the next day, at which time all were euthanized.

It would be expected that use of this *salmonella* strain (triple mutant) as a vaccine, or the creation of similar strains of *Yersinia, Shigella, E. coli*, or *Campylobacter*, or even other *salmonella* species would also give such a protective affect against shigellosis, yersinial infections (enterocolitis or bubonic plague), campylobacteriosis, or a wide range of *E. coli* infections of the urinary tract or other tissues. These would apply to human infections as well as to livestock.

Probably the most likely use of these stains would be to prevent diarrheal illnesses and typhoid fever. It is likely that the virulent strains never pass the mesenteric lymph nodes to overwhelm the host, if the host is first challenged with the strain unable to use $H_2$.

Example 4

*Helicobacter hepaticus* Deficient Hydrogenase Mutants

In recent years, more than three different *Helicobacter* species have been recovered from rodents with *H. hepaticus* being the most well studied enterohepatic *Helicobacter* species. First isolated in 1992 from untreated A/JCr control mice, *H. hepaticus* is a Gram negative, microaerophilic bacterium that occurs naturally in many strains of inbred mice. Mice infected with this bacterium develop chronic hepatic lesions and are more prone to developing hepatocellular carcinoma which has made *H. hepaticus* an excellent model for studying mechanisms of bacterial-associated liver carcinogenesis. Although *H. hepaticus* can be isolated from the liver of infected mice, it is more consistently recovered from the intestinal tract since the primary site of colonization is the lower bowel of mice.

As described in Example 1, hydrogenase was demonstrated to be important for colonization of the animals. As described herein the physiological role of this enzyme in *H. hepaticus* has now been investigated. The colonization deficiency of hydrogenase structural gene mutants of *H. pylori* was attributed to their inability to utilize hydrogen as an energy substrate. *H. hepaticus* hydrogenase is also a hydrogen-uptake hydrogenase which can oxidize molecular hydrogen to yield protons and electrons; the low-potential electrons can enter the electron transport chain and thus help in energy conservation. The hydrogen content in the liver of live mice is comparable to that in the stomach (~50 μM), but in the small intestine, the hydrogen content is almost four-fold higher than in the stomach. The whole cell Km of *H. hepaticus* hydrogenase for hydrogen is around 2.5 μM, making it a high affinity enzyme. The source of hydrogen in the animal tissues is attributed largely to the fermentation reactions leading to formation of acetate and butyrate with hydrogen as a byproduct due to necessity of electron disposal.

To investigate whether the energy-conserving role of hydrogenase is useful for colonization of *H. hepaticus*, a mutant strain was generated in the structural gene (hyaB) encoding for the large subunit of hydrogenase. This mutant strain was compared to the wild type for physiological and colonization abilities. Histopathological studies of the infected tissues were also carried out to compare the pathological effects caused by the wild type and the mutant.

Materials and Methods

Bacterial strains and growth conditions. *H. hepaticus* strain ATCC 51449 and *Escherichia coli* DH5α (BRL) were used for genetic manipulations. *H. hepaticus* was grown on *Brucella* agar plates (DIFCO) supplemented with 10% defibrinated sheep blood (BA) with either chloramphenicol (30 μg/ml), or without any antibiotics. Plates were incubated microaerobically at 37° C. in an incubator (5% CO2 and 1% O2). Broth experiments (growth and amino acid uptake studies) were performed in Mueller Hinton broth (MHB) with either 2 or 5% fetal bovine serum (FBS) in bottles with gas-controlled environment. The atmosphere contained 85% N2, 5% CO2 and 10% H2. *E. coli* was grown on Luria-Bertani medium supplemented with ampicillin (100 μg/ml), or chloramphenicol (30 μg/ml) and grown at 37° C. aerobically. Fecal and tissue samples were plated on BA medium with amphotericin B (10 μg/ml), vancomycin (10 μg/ml) and cefoperazone (20 μg/ml).

Figure 4:
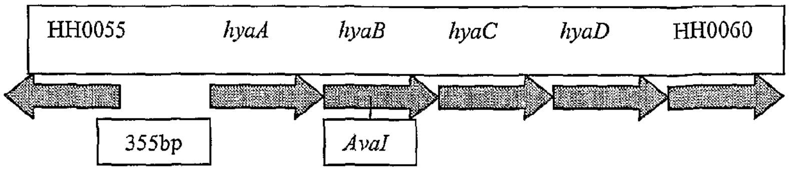
FIG. 4 is a schematic representation of the organization of hyaB gene in the genome of *H. hepaticus*. Four hydrogenase structural genes, hyaA, hyaB, hyaC and hyaD (HH 0056 to HH 0059) are present in a single operon. The distance between HH 0055 (traA_2) and hyaA is 355 bp and it is transcribed in the reverse orientation. HH 0060 is a hypothetical gene. Partial sequence of hyaB and hyaC (1303 bp) was PCR amplified and cloned into a pGEM-T vector followed by insertion of a chloramphenicol resistance cassette into an unique AvaI site within hyaB to give the pGEM-T:hyaB:Cm construct.

Construction of *H. hepaticus* hyaB (HH 0057) and mutant strain by insertional mutagenesis. The hyaB gene which encodes for the large subunit of hydrogenase lies between hyaA (which encodes for the small subunit of hydrogenase) and hyaC (which encodes for a cytochrome oxidase, part of the hydrogenase operon) (FIG. 4). The downstream gene hyaD is also a part of the hydrogenase operon since it is an orthologue of the hydD gene of *H. Pylori* shown to be required for synthesis of hydrogenase. Primers hyaBF (5' ttcgtggtatgaggataatcagcc-3'; SEQ ID NO: 18) and hyaBR (5' aataaagcacaactcccgtgagag-3'; SEQ ID NO: 19) were used to PCR amplify a 1303-bp fragment using wild type *H. Hepaticus* ATCC 51449 genomic DNA as template. This fragment contained partial sequences of hyaB and its adjacent gene, hyaC. The PCR fragment was ligated into pGEM-T vector (PROMEGA) following the manufacturer's instructions. The cloned construct was obtained by transforming the ligation mixture into *E. coli* DH5α. Subsequently, a chloramphenicol (Cm) resistance cassette was inserted into a unique AvaI site within hyaB giving the construct, pGEM-T:hyaB:Cm. The recombinant plasmid was introduced into *H. Hepaticus* by electrotransformation (pulse of 2.5 kV in a transporator plus apparatus, BTX). As a result of allelic exchange, the hyaB mutant strain was obtained.

Hydrogenase assays of wild type and hyaB mutant strain. Since the mutation was within the large subunit of hydrogenase, the strain was assayed for hydrogenase activity using an amperometric method (Maier et al., (1996) FEBS Microbiol Letters, 141: 71-76). Even if the mutation had been polar, it would only affect the hydrogenase activity since the downstream genes are also part of the hydrogenase operon. Nickel has been shown to be required for the post translational processing of the large subunit of hydrogenase in *E. coli, Alcaligenes eutrophus, Bradyrhizobium japonicum* and other bacteria since the catalytic activity of hydrogenases depends on the presence of nickel in its active site. *H. hepaticus* wild type and hyaB mutant strains were grown on BA media supplemented with different concentrations of NiCl2 (0, 1, 2, 6, 8, 10 and 20 μM) to address possible differences in the hydrogenase and urease activities as the nickel concentration (supplementation) was varied. Plates were incubated at 37° C. in an anaerobic jar sparged with anaerobic gas mixture (10% H2 and 5% C02 balance N2). Whole cells were used for the assay, with O2 provided as the final electron acceptor (Table 3).

Figure 5:
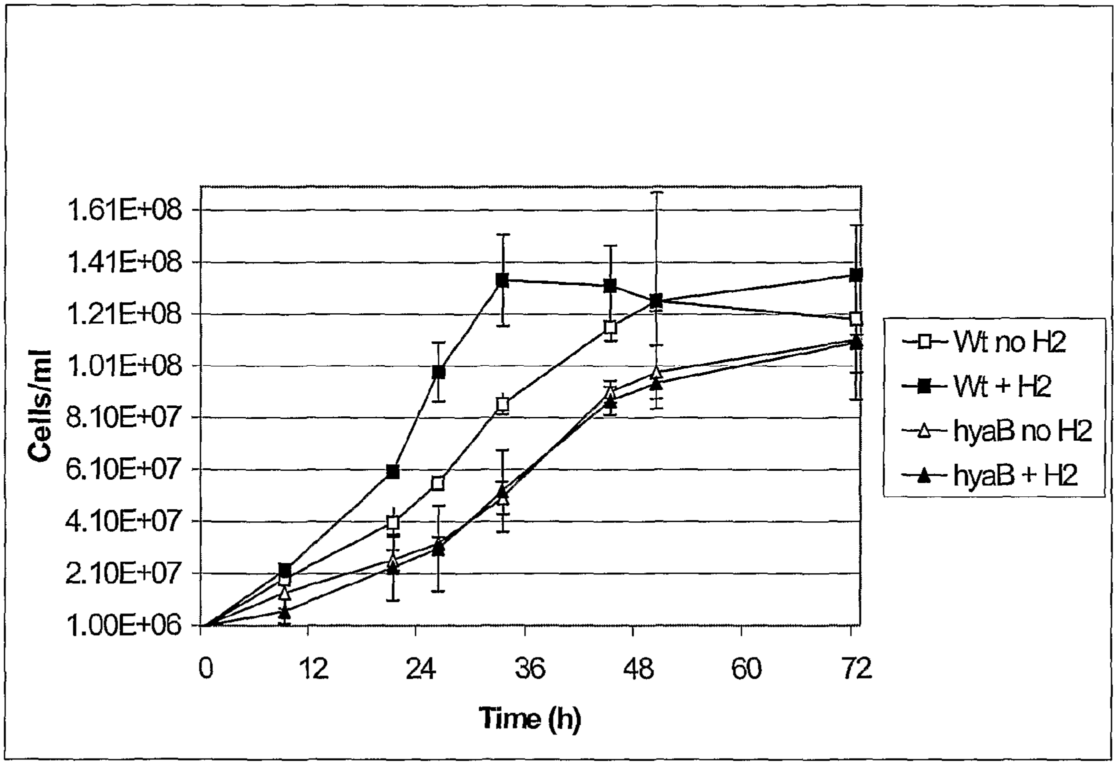
FIG. 5 is a graphic presentation of data showing growth of wild type and hyaB mutant in the presence of 10 μM supplementary nickel and in the presence or absence of hydrogen. Results are representative of three independent experiments, all conducted in MHD plus 2% serum. The gas (either $H_2$ or argon) was added to 10% of the head space atmosphere, delivered through a serum stopper via an argon-sparged syringe, from a 100% tank of the indicated gas.

Growth of wild type and hyaB mutant in the presence and absence of hydrogen. Initial experiments indicated that growth of the strains in liquid medium was facilitated by the addition of (up to 10 μM) nickel, but such stimulation was variable and could not be attributed to the Ni-hydrogenase enzyme as such stimulation was observed in both the parent and the hyaB strain. In order to study the effects of hydrogen on the growth, the wild type and hyaB mutant strains were grown in the presence of 10 μM NiCl2 and with 10% argon versus with 10% hydrogen added. Serum bottles containing Mueller Hinton broth (MHB) were sparged with N2 to expel all the air. CO2 (5%), O2 (2%) and H2 (10%) or argon (10%) were injected into the bottles (v/v of the head space). After autoclaving, fetal bovine serum (FBS) and NiCl2 solution (10 μM) were injected. In some experiments 2% serum was used, in others 5%, as indicated in the text or Brief Description of the Drawings. All the growth and amino acid uptake experiments were performed with 5% serum initially. After it was determined that use of a lower serum level (2%) facilitated H2-dependent studies (see below), all (growth and amino acid transport) experiments were repeated with that serum level as shown. The increase in growth was measured spectrophotometrically (A600) and is expressed as absorbance units (OD) (FIG. 5). OD was converted to cells/ml using a standard curve based on a direct (microscopic) counting approach (Maier et al., (2003) J Bacteriol 185: 2680-2682). From this curve an OD of 1.0 is approximately equal to 1.6×109 cells/ml of the broth medium. The growth abilities of both the wild type and mutant strain, were reduced by supplementing the medium with 20 μM nickel.

$^{14}C$ labeled amino acid uptake ability of hyaB mutant and wild type. In order to investigate whether membrane-bound hydrogenase can use hydrogen as an energy substrate for uptake of amino acids, *H. hepaticus* wild type and hyaB mutant cells were grown overnight on a shaker at 37° C. in MHB with 2% FBS in 160 ml serum bottles, four bottles per strain. These tightly sealed bottles were previously sparged with N2 to expel all the air and injected with 2% O2 and 5% CO2 (v/v of head space). After the OD600 reached 0.08, 10% H2 (v/v of head space) was injected into two of the bottles for each strain and 10% argon (v/v of head space) into the other two. After 2 hrs, $^{14}C$ uniformly-labeled amino acids (Amersham Biosciences AMERSHAM BIOSCIENCES CFB 104, specific activity in the medium within the serum bottles was 1.0 μCi/ml. For the 0 hr time reading, 2 ml of the culture suspension was immediately withdrawn from the bottles (after injecting the label and mixing solution) using a sterile syringe, and four separate samples (2 ml) were added to wells of a filtering manifold unver vacuum. The filter used was 0.22 μm membrane (MILLIPORE, GSWP 02500). After filtering the cell suspension, the membrane was washed with two separate 1 ml aliquots of sterile phosphate buffered saline (PBS) pH 7.2 to wash off the $^{14}C$ amino acids externally adhering to the cells, and then the membranes were transferred into individual scintillation vials. Five ml of the fluor (SCINTIVERSE, Fischer Scientific) was added. Scintillation spectrometry was done as described previously (Maier et al., (1988) J Bacteriol 170: 1986-1989). The background level uptake of $^{14}C$ amino acids (at 0 hr) was estimated after averaging the four separate 2 ml samples. After background sampling, the bottles were allowed to shake at 37° C. for 2 and 5 hr, and 2 ml samples (total of 8 replicate samples) of the culture suspension were taken and filtered as described above. The average cpm/2 ml of filtered cells at 0 hr was subtracted from the averaged 2 and 5 hr time points, resulting in the data shown in Table 4.

For studying whole cell kinetic parameters, a series of limiting substrate levels ($^{14}C$ amino acids) were added to 10 ml volumes of cells in sealed (60 ml) vials. The level of activity (substrate) added ranged from 1.0 μCi/ml to 0.04 μCi/ml (nine different concentrations were used) of cell suspension. The cells had been pre-grown to an $OD_{600}$ of 0.08 as described above, and then $H_2$ added for the 2 hr period (10% v/v of head space) in tightly sealed bottles previously sparged with $N_2$ to expel all the air and also injected with 2% $O_2$ and 5% $CO_2$ (v/v of head space). The cells were transferred to the 60 ml vials (containing the same atmosphere as above) by use of argon-sparged syringes. Therefore, the cells never suffered an $O_2$ shock or a change in gas ($H_2$ or argon) composition exposure during the (20 min) uptake assay. For kinetics, the transport assay was performed within the linear uptake activity time frame of incubation with substrate. The incubation with substrate proceeded for 20 min, and four 2 ml samples were individually filtered and $^{14}C$ measured as described above. Filtered samples from the medium alone with the individual label activity were averaged and subtracted from the experimental (cells) samples. The half saturation affinity and the maximum velocity of the uptake was estimated from a linear transformation of the data in the form of a double reciprocal plot yielding a line equation of y=bx+a. The y-intercept parameter (variable a in the equation) for each strain is reported in the text. A saturation constant in terms of Km cannot be assigned to the data, as the serum already contains amino acids at an unknown level, but relative half-saturation affinities and Vmax for the wild type compared to the mutant could be accurately estimated.

Mice infection. Six week old inbred male A/J mice, certified to be *Helicobacter*-free (routinely tested for absence of *H. hepaticus, H. bilis* and *H. muridarum*) were obtained from Jackson laboratories (Bar Harbor, Me.). They were housed with autoclaved food, water, bedding and were quarantined from other experimental animals. Cage changes were performed in a laminar flow hood. Animals were housed in groups of four per microisolator cage.

*H. hepaticus* wild type or mutant strains were grown for 72 hours on BA plates and harvested by centrifugation with one wash step in PBS, pH 7.2. The OD of the inoculum was adjusted to 0.32 at 600 nm, which is approximately equivalent to $5\times10^8$ cells/ml (16). The suspension was maintained in argon-sparged buffer to minimize oxygen exposure. Two doses (0.2 ml each) of this suspension of the wild type or the hyaB mutant culture were administered to each mouse by oral gavage on alternating days. Ten mice were inoculated for each bacterial strain. Six control mice were sham inoculated with 0.2 ml of sterile PBS on alternating days. Fecal pellets were sampled from the cages after completion of 20 weeks. After 21 weeks the mice were euthanized and the liver and cecum were excised for qualitative, quantitative and histopathological analysis. The proximal colon was excised only for histopathological testing.

Qualitative analysis of liver, cecum and fecal samples. 200 mg of fecal pellets collected from the cages at 20 weeks post inoculation were homogenized in 5 ml of sterile PBS. The suspension (200 μl) was plated on BA plates with triple antibiotic (amphotericin B (10 μg/ml), vancomycin (10 μg/ml) and cefoperazone (20 μg/ml). The plates were kept in a microaerobic incubator (1% $O_2$, 5% $CO_2$) at 37° C. for 72 to 96 hrs. Presence of *H. hepaticus* was confirmed by microscopy, catalase test and by PCR.

Mice were euthanized 21 weeks post inoculation and the liver and cecum were excised. Liver (left, right, caudate and part of the median lobe) and cecum (entire tissue after taking out sample for histopathology), were first homogenized using a tissue tearor (BIOSPEC Products, Inc., Bartlesville, Okla.). The homogenized tissue suspensions (200 μl) were plated on BA plates with triple antibiotic to check for the presence or absence of *H. Hepaticus*. Growth, if present, was confirmed by microscopy, catalase test and by PCR. Part of the median lobe of the liver was used for hisotpathology.

Quantitative analysis of liver and cecum. It is commonly acknowledged that counting colonies of *H. Hepaticus* is a challenging protocol, as the colonies tend to stick to one another, and to spread out over the plate. Hence, we performed a real time PCR to quantify *H. hepaticus* in the tissues. In addition, real time PCR is a rapid and sensitive technique which has been used to amplify and detect *H. hepaticus* DNA from tissue isolates of infected mice. Following homogenization of the liver and cecum, the DNA was extracted from 25 mg of the tissue using the Dneasy tissue kit (QIAGEN). Quantitative analysis was performed by real time PCR (iCycler Thermal cycler, BIO-RAD) using H. Hepaticus specific cdtB primers (cdtBF 5'-GGCTAGATACAA-GAATCGCTAAT-3'; SEQ ID NO: 20 and cdtBR 5'-CTAC-CTACTACCGCATAATCAAG-3': SEQ ID NO: 21) which produce a 109 bp amplicon. Specific primers and probe were designed using the Beacon Designer Software (version 3.0, BIO-RAD). Primers and probe for the cdtB gene (encoding for subunit B of the cytolethal distending toxin) were shown to be highly specific for *H. hepaticus* by doing a BLAST against known genomes.

Real time PCR analysis was performed by using a 50 μl admixture containing 25 μl of iO SUPERMIX (BIO-RAD), 200 nM each of cdtF, cdtR primers, cdtB probe and 10 μl of tissue DNA (equivalent to 1.25 mg tissue). Conditions for real time were 1 cycle at 95° C. for 3 min, 40 cycles each of 95° C. for 30 s and 58° C. for 30 s. Samples ranging from 102 to 107 femtograms of *H. hepaticus* genomic DNA was used to generate a curve. From the standard curve of threshold cycle v/s log starting quantity in femtograms, the amount of DNA in the unknown tissue samples was estimated and converted to the number of copies of *H. hepaticus* genome using the following calculations:

The genome size of *H. hepaticus* is 1.8 Mbp which is equivalent to $11.88\times10^8$ g/mol (since 1 bp=660 g/mol). According to Avogadro's number, 1 mol of any substance contains $6\times10^{23}$ molecules. So $11.88\times10^8$ g will contain $6\times10^{23}$ molecules, or 1 g will contain $5\times10^{14}$ molecules; therefore 2 fg DNA will be equivalent to 1 molecule or 1 copy of the *H. hepaticus* genome.

Histopathology studies. The tissue samples measuring about 1 cm×1 cm (median lobe of liver, cecum and proximal colon) were fixed overnight in 10% buffered formalin, and were routinely processed and embedded in paraffin. 5 μm thick sections were stained with hematoxylin-eosin stain and were graded semi quantitatively for different histological parameters as described: fibrosis (0, absence; 1, mild portal fibrosis; 2, portal fibrosis with occasional periportal changes; 3, bridging fibrosis; 4, cirrhosis), portal inflammation (0, no inflammation; 1, mild infiltrate in minority of portal tracts; 2, mild infiltrate in almost all portal tracts; 3, moderate infiltrate in most portal tracts; 4, severe infiltrate in most portal tracts), lymphoid nodules in portal tracts (0, no nodules; 1, nodules occasionally present; 2, nodules in majority of portal tracts; 3, large nodules in all portal tracts), biliary lesions (0, no lesions; 1, occasional or mild cholangitis; 2, severe cholangitis), lobular inflammation and/or necrosis (0, absence; 1, moderate) and tumors (0, absence). The lobular inflammation scores (including hepatocytic coagulative necrosis) that were positive were further sub-ranked for subjection to a Wilcoxin rank test, based on their inflammation ranking. For example, the first 8 rankings (all wild type samples) were listed first in the sequential rank, and then the remaining 12 rankings (no inflammation) were equally weighted among the two wild type and ten mutant samples, as is permitted by the Wilcoxin test. Among the 20 rankings, the ten assigned to the wild type are compared against the 10 mutant strain assignments for statistical ranking comparison. This statistical test, which clearly demonstrated a difference in lobular inflammation between the wild type and the mutant strain was not applied to the other histopathology data, and no statistical differences are claimed for that data.

Results

Insertional mutagenesis of hyaB gene. The disruption of the hyaB gene was confirmed by PCR, as an increased size of the PCR product on an agarose gel (2150 bp for the hyaB mutant versus 1303 bp for the wild type). The chloramphenicol resistance cassette was inserted in the same direction as the hyaB gene; the organization of the genes involved and the $Cm^r$ construct are depicted in FIG. 1. To establish that these two mutations are non polar, an ideal method would be to carry out complementation studies, but there are limitations to the genetic techniques presently available to manipulate *H. hepaticus*. Nevertheless, based on the annotated sequence the only genes expected to be interrupted even if the insertion is polar, are ones related to hydrogenase-specific enzyme maturation.

*H. hepaticus* colonies tend to merge with each other, thus it is quite rare to obtain isolated colonies upon plating. However the number of transformants obtained was extremely low for introducing hyaB mutations: only two or three transformant colonies were obtained per $10^8$ to $10^9$ cells. However, as the number of transformants was very few, the margins of each colony could be easily differentiated from one another on the BA plate.

Nickel affects on hydrogenase and urease activities in the wild type and the hyaB mutant. The catalytic activity of bacterial uptake hydrogenases depends on the presence of nickel at the unique active site. A battery of nickel transport and metal accessory proteins facilitate nickel insertion into the NiFeS-center. Similarly, urease is a nickel-containing enzyme, requiring Ni-dependent maturation machinery. Nickel supplementation has been shown to facilitate urease activity in *H. pylori*, but hydrogenase enzyme activity does not increase significantly in response to nickel supplementation of the medium. We observed more than a 25-fold increase in urease activity in the presence of 10 μM added nickel vs without nickel supplementation for both (hyaB and wild type) bacterial strains (see Table 3). Even a 1 μM nickel supplementation increased urease activity 7-fold over no supplementation, and this was a statistically significant difference (see Table 3). Similar (nickel stimulation) of urease activity values were observed for the hyaB mutant as for the wild type. The comparative growth affects by nickel supplementation versus without nickel supplementation (doubling times varied between 7.5 and 11.5 hrs, in the absence of $H_2$) were too variable to clearly interpret, perhaps due to variations in the nickel content of the medium.

Hydrogenase activities of the wild type *H. hepaticus* strain also increased significantly with increasing concentrations of supplemented nickel in the medium (Table 3). Activity decreased (for both hydrogenase and urease) above 10 μM and 8 μM nickel, respectively, perhaps due to toxicity at the higher nickel concentrations. Similarly, growth was inhibited at nickel levels above 10 μM $NiCl_2$ supplementation. For subsequent growth experiments (see text below) and to study the hydrogenase-specific affects, subsequent experiments (such as amino acid transport) always included 10 μM nickel in the medium within the closed gas atmosphere. The hyaB strain completely lacked hydrogenase activity even in the presence of externally added nickel (Table 3 legend), as expected due to the disruption of the (hyaB) structural gene.

Uptake of $^{14}C$-labeled amino acids by the wild type and the hyaB mutant. Most $H_2$ oxidizing bacteria are chemoautotrophs, using the energy from $H_2$ to fuel the energy input needed for carbon dioxide fixation. The $CO_2$ fixation enzymes are highly conserved. However, no such $CO_2$ fixing enzymes exist in the *Helicobacters*, based on the annotated genome sequences of (two) *H. pylori* or (one) *H. hepaticus* strains. Therefore it is expected the energy form $H_2$ may be used to assimilate non-$CO_2$ sources of carbon. The amino acid uptake ability after 2 and 5 hr by the wild type cells in MHB with 2% fetal bovine serum and in an $H_2$-containing atmosphere was 7-fold and 6.5-fold greater respectively, than the wild type in argon (all data summarized after subtracting the 0 hr reading). The amino acid uptake level at 2 hr and 5 hr by the wild type cells in hydrogen was 6 and 5.5-fold more respectively, than for the hyaB mutant strain in the presence of hydrogen (Table 4). As expected, if the transport rate was markedly facilitated by hydrogen oxidation, the mutant strain had the same (low) level in the presence of hydrogen or argon. The difference between the wild type and mutant or between the $H_2$ versus argon condition (for the wild type) was less pronounced when the same experiment was done but with 5% serum in the medium. Only an approximately 2-fold difference ($H_2$ stimulation when comparing $H_2$ versus an argon atmosphere) was observed in amino acid uptake (2 hr time point) when the cells were grown in the higher serum content medium (see Table 4, legend). It is possible that $H_2$ use may be most beneficial when the cells exhaust other available substrates.

TABLE 3

Hydrogenase and urease activities of the wild type strain grown on different levels of nickel supplementation.

| Nickel Concn ($\mu$M) | Hydrogenase activity (nmol $H_2$ oxid/min/$10^8$cells) | Urease activity ($\mu$mole $NH_3$/min/mg protein) |
|---|---|---|
| 0 | 0.4 ± 0.02 | 0.07 ± 0.01 |
| 1 | 0.8 ± 0.1 | 0.5 ± 0.03 |
| 2 | 1.5 ± 0.1 | 0.8 ± 0.08 |
| 6 | 1.7 ± 0.2 | 1.0 ± 0.08 |
| 8 | 2.0 ± 0.2 | 2.3 ± 0.1 |
| 10 | 2.6 ± 0.2 | 1.8 ± 0.2 |
| 20 | 1.8 ± 0.3 | 1.7 ± 0.1 |

All results are average ± SD of five readings, and the experiment was repeated two additional times with similar results. According to students t-test, the results for each nickel concentration are significantly greater than the previous lower nickel concentration tested at $P < .05$, with the exception of the 10 versus 20 $\mu$M, and the 2 $\mu$M versus 6 $\mu$M levels for hydrogenase, and for the levels above 8 $\mu$M nickel for urease.

TABLE 4

Uptake of $^{14}$C-labeled amino acids by the wild type and the hyaB mutant strain in MHB containing 2% serum.

| Strain | Incubated with | $^{14}$C amino acid uptake at 2 hr (cpm × $10^2$/ $10^8$ cells) | $^{14}$C amino acid uptake at 5 hr (cpm × $10^2$/ $10^8$ cells) |
|---|---|---|---|
| Wild type | $H_2$ | 64 ± 8 | 102 ± 7 |
| Wild type | Ar | 8.6 ± 2 | 15.7 ± 5 |
| hyaB mutant | $H_2$ | 9.2 ± 3 | 18.5 ± 2 |
| hyaB mutant | Ar | ND | 18.3 ± 3 |

The cpm/$10^8$ cells from uniformly labeled amino acids taken in a 2 hr and 5 hr period is shown. The wild type strain results in hydrogen are significantly greater than in argon at $P < 0.05$ according to Students t-test analysis. The wild type strain results (in the hydrogen-containing atmosphere) at the 5 hr sampling time is also statistically significantly greater ($P < 0.05$) than that for the mutant strain. Results are averaged from 8 values (±SD) from one experiment, but a second experiment showed similar results. In the same medium, but containing 5% serum, the 2 hr wild type values (cpm × $10^2$/$10^8$ cells) were 6.6 ± 2 (argon) and 14.7 ± 3 ($H_2$), respectively. These latter samples were also statistically significantly different than each other and were taken at the same cell density ($OD_{600}$ of approximately 0.1) as for the 2% serum results.

Maximum uptake rates and kinetics of amino acid transport. The whole cell amino acid uptake kinetic parameters were compared between the parent strain and the hyaB mutant with both strains; this was determined for both strains incubated with 10% $H_2$ provided during the assay. These kinetic assays to determine half saturation affinity and Vmax are normally applied to substrate use by enzymes, but such determinations have been useful to correlate whole cell substrate use characteristics of *H. pylori* to in vivo virulence characteristics. Also, with regard to $H_2$-oxidation mediated affects, it was shown that $H_2$ use by *Azotobacter vinelandii* increased the bacteriums Vmax for mannose uptake without altering the bacterium's affinity for the substrate. In short term assays of amino acid uptake with a series of (including limiting) substrate concentrations, the double reciprocal linear transformation of the data yielded a line equation in the form of y=bx+a, where a, the inverse of the Vmax was determined to be 0.279 for the parent strain and 0.605 for the mutant. This difference was statistically significant ($P<0.05$) as the linear transformation plot was based on four replicate samples at each of nine different substrate concentrations for each strain. Therefore the Vmax for the wild type for amino acid transport is about 2.2 fold more than for the mutant strain. However, the half saturation affinities calculated from the slope parameter (b in the above equation) were similar for both strains. From this result it appears that $H_2$ augments the transport rate, but it likely does not cause synthesis of new amino acid transport components with a higher affinity for the carbon/nitrogen-containing substrates (i.e. amino acids).

Growth of the wild type and hyaB mutant in the presence and absence of hydrogen. As was described for *H. pylori, H. hepaticus* hydrogenase activity was also determined to be constitutively expressed in rich medium (MHB plus serum), irrespective of whether the cells are grown with (10% partial pressure $H_2$ added to gas phase) or without added $H_2$ (argon substituted for $H_2$). Still, for *H. pylori*, maximum hydrogenase activities achieved were greater in cells grown with $H_2$ than without the gas. For *H. hepaticus*, activities achieved in MHB plus serum were the same (in nmoles/min/$10^9$ cells, mean±std. dev. for 5 replicates) with $H_2$ (41±4) as when cells received 10% argon instead of $H_2$ (42±5). These whole cell activities are considerably greater than previously reported; this discrepancy was investigated and found to be due to the combination of using liquid cultures and MHB medium rather than a blood-based medium used previously. Nevertheless, the growth rate of the wild type *H. hepaticus* in the presence of hydrogen was significantly better (lower doubling time) than when argon replaced $H_2$ as 10% of the atmosphere (see FIG. 5).

This difference in growth was observed in 3 separate experiments, with each time point assayed 3 times for each experiment. For all three separate experiments, the maximum growth rate achieved in $H_2$ for the wild type was approximately two times (doubling time in hr of 4.2±0.7 for $H_2$ and 8.4±1.4 for argon) that of the same culture condition but lacking $H_2$ (argon replaced hydrogen); this growth rate was statistically significantly different ($P<0.05$) among the two values (argon compared to $H_2$) for the wild type and also between the wild type in $H_2$ compared to either of the two atmospheric conditions applied to the hyaB strain. Not surprisingly, growth of the mutant strain was unaffected by $H_2$, and was lower than for the parent strain (FIG. 5). As was observed for the amino acid uptake studies, this growth stimulation affect by $H_2$ was less pronounced when 5% serum was used (data not shown). Nevertheless, it was observed that the serum level (2% versus 5%) used did not significantly affect the whole cell hydrogenase activities achieved (data not shown). The maximum doubling times for the hyaB strain with or without $H_2$ (FIG. 5) was about 12±3 hr; this may be less than for the parent strain in the absence of $H_2$ (8.4±1.4 hr) if many growth experiments are performed to obtain sufficient replicates for rigorous statistical analysis. Should this be indicated, it is conceivable that the parent strain (even without $H_2$ added) gleans a growth advantage over the mutant due to fermentative enzymes producing small amounts of $H_2$ as a byproduct of microaerobic/anaerobic metabolism.

Qualitative analysis of *H. hepaticus* in feces, liver and cecum. *H. hepaticus* was recovered from liver and cecum homogenates (at 21 weeks after inoculation), as well as from fecal suspensions (at 20 weeks) from each mouse inoculated with the wild type or hyaB or mutant strain. Growth observed on BA plus three antibiotics was confirmed to be that of *H. hepaticus* by microscopy, catalase test and by PCR (data not shown). Tissue homogenates and fecal suspensions from control (uninoculated) mice did not show growth of *H. hepaticus* on any of the plates.

Quantitative analysis of liver and cecum. Colonization efficiency of the wild type and the hyaB mutant strain was approximated using real time PCR. A standard curve was used for estimating the femtograms of DNA, which was later converted to genome copy numbers (data not shown). Results of real time analysis showed comparable genome copy numbers in the liver and cecum from the mice inoculated with either strain after 21 weeks. The average genome copy (from 10 mice for each strain) among all samples (each determination from 1.25 mg of tissue) ranged from $1.2\times10^3$ to $1.8\times10^3$ (liver), or from $1.4\times10^6$ up to $1.9\times10^6$ (cecum). The results were not statistically different among the two test strains. These results indicated that expression of hydrogenase may not important be for *H. hepaticus* colonization of the mouse liver or the cecum. No *H. hepaticus* DNA was detected in tissues of control mice.

Histopathology results. The animal colonization attributes of many *Helicobacters* (including by *H. hepaticus*) have been well documented and reviewed. At necropsy, gross examination of liver, intestines and other visceral organs revealed no significant lesions in any of the mice tested. Fibrosis, lymphoid nodules or tumors were absent in the liver of all the inoculated mice. Biliary epithelial and oval cell changes were absent in all mice (10 animals for each bacterial strain) but one mouse inoculated with the wild type showed mild biliary hyperplasia. Mild portal infiltration consisting of lymphocytes and plasma cells in some of the portal region/areas within the hepatic lobules was observed in six wild type-inoculated mice, and moderate infiltration in almost all portal areas was observed in one (wild type inoculated) mouse. Very mild portal infiltration in a few of the portal areas was observed in eight hyaB-inoculated mice but also in 3 of the six uninoculated animals. The latter (uninoculated controls) had no evidence of degeneration, inflammation, or necrosis, or neoplasm and all were negative for *H. hepaticus* by real time PCR analysis of liver and cecum.

A clear difference between the mice inoculated with the wild type and the hyaB mutant was seen in lobular inflammation. Most (8 of 10) of the wild type inoculated mice showed moderate lobular inflammation (lymphoplasmacytic hepatitis) with hepatocytic coagulative necrosis, and this was statistically highly significantly different (at $P<0.01$, according to Wilcoxin rank analysis) than for the hydrogenase mutant, for which no mice exhibited those characteristic hepatic lesions; none of the ten mice inoculated with the hyaB mutant showed any evidence of lobular inflammation or necrosis. There was no histological evidence of lesions in the cecum or the proximal colon for any test group, and control mice had no histological evidence of lesions in the liver, cecum or the proximal colon. Another control was provided by another *H. hepaticus* mutant strain, but in the oxidative stress-combating enzyme alkylhydroperoxide reductase (all details about that strain will be described in detail elsewhere). That strain, containing an antibiotic resistance cassette in the chromosome of the tsaA gene (HH#1544) showed wild type-like necrotizing hepatitis when tested for pathology characteristics alongside the parent and the hyaB strain (ten mice also used for the tsaA strain) as described herein.

Discussion

The vast majority of *Helicobacter* research involves the gastric pathogen *H. pylori*. However, many intriguing *Helicobacter* species exist in animals, and physiological and virulence studies of *H. hepaticus* have become increasingly important due to the association of this enterohepatic *Helicobacter* species with chronic hepatitis in mice and due to the increased incidences of hepatocellular carcinoma in these infected animals. *H. hepaticus* thus serves as an excellent model for studying liver carcinogenesis.

In order to investigate the role of hydrogenase in the colonization and virulence of *H. hepaticus*, a mutant strain was generated in the gene encoding the large subunit of hydrogenase (hyaB). The wild type strain possessed hydrogenase activity and the activity increased when the cells were grown in the presence of supplemented nickel. Nickel significantly stimulated the activity of both key Ni-enzymes (urease and hydrogenase), and this stimulation affect is greater than is observed for *H. pylori*. This difference in the two *Helicobacters* could be related to the histidine rich nickel-binding protein present in *H. pylori* (Hpn and Hpn-like protein), which would be expected to serve as storage reservoirs for nickel; both of these histidine rich proteins are absent in *H. hepaticus*. Therefore, *H. hepaticus* may depend greatly on exogenous nickel. As expected due to the absence of the hydrogenase structural gene, nickel supplementation could not restore the hydrogenase activity to the hyaB mutant, yet nickel supplementation stimulated urease activity in the mutant like in the parent strain.

In vitro studies showed that liquid growth in the presence of hydrogen (doubling time) of the wild type strain was better than that for the hyaB mutant, most likely due to the ability of the wild type to use hydrogen as an additional energy substrate for growth. Growth stimulation due to supplying $H_2$ to diverse $H_2$ oxidizing bacteria has been observed previously, but has not been reported for pathogenic bacteria.

Wild type cells had much increased ability for uptake of $^{14}C$ amino acids in the presence of hydrogen, than in the absence of hydrogen, or when compared to the hyaB mutant cells either in the presence or absence of hydrogen. This is likely due to wild type cells gleaning energy from hydrogen that is coupled to amino acid transport. From the *H. hepaticus* sequence it is clear that this bacterium, like *H. pylori*, has abundant amino acid transport systems. $H_2$ stimulation of both growth and amino acid uptake was most evident when 2% serum was used rather than 5%; this could indicate that hydrogenase may be most important to the bacterium as an alternative energy source when nutrient conditions are diminished. The Vmax value expressed by the wild type (in $H_2$) for amino acid transport was 2.2-fold greater than for the mutant strain. This would be consistent with $H_2$ providing an energy source (perhaps ATP) to augment uptake rates. Still, the half saturation affinities for amino acid uptake were similar for the parent and the mutant. From this latter result it appears that although $H_2$ stimulates transport, it likely neither causes synthesis of new amino acid transport components with a higher affinity for the carbon substrates, nor preferentially enables higher affinity uptake systems to be used.

It may appear from real time analysis estimates of genome number (and thereby comparative colonization) by the wild type and hyaB mutant that there is no growth advantage due to $H_2$ use within the liver or cecum. This is surprising in light of the other results, and suggests that hydrogen may be only one among many growth substrates utilized by *H. hepaticus* within the tissues. Therefore, demonstrable growth advantages in vivo due to hydrogen are unrealized. If the tissues (especially liver) are well supplied with carbon and energy sources this would be consistent with the idea proposed above that $H_2$ use may be most important under low nutrient conditions. Nevertheless, a clear difference was seen in the photomicrographs of the liver of mice inoculated with the hyaB mutant versus the wild type or another *H. hepaticus* mutant strain; these results showed complete absence of lobular inflammation by the hyaB mutant (and similar to uninoculated control mice results), while liver from 8 out of 10 mice inoculated with the wild type showed moderate inflammation with necrosis. Although hydrogenase may not be directly responsible for the pathogenesis seen in the liver tissue of mice inoculated with the wild type, the highly diffusible high energy reductant is present in liver tissue of live mice, and energy released by hydrogen oxidation may be used to augment synthesis of virulence-related proteins or enzymes responsible for causing inflammation and necrosis. Possibly high efficiency solute uptake systems (such as for amino acids) that are supported by $H_2$ oxidation may be coupled to virulence.

This is the first evidence of the involvement of molecular hydrogen use via hydrogenase in the development of one of the bacterial-dependent symptoms of hepatitis, namely inflammation and necrosis of the liver tissue. Therefore this study adds *H. hepaticus* to the list of bacteria (including for example *H. pylori* and *Salmonella typhimurium*) that use hydrogen to augment their virulence in animals. It is noteworthy that insertion cassette mutagenesis was successful for *H. hepaticus* mutagenesis and it is anticipated that this procedure can be used by many researchers for studying roles of other genes in this and other bacterium.

The invention claimed is:

1. An isolated bacterium wherein said isolated bacterium is *Salmonella typhimurium*, wherein the isolated bacterium does not express a functional NiFe hydrogenase protein, wherein the isolated bacterium comprises a deletion mutation to each of three NiFe hydrogenase genes present in the genome of the isolated bacterium, wherein each mutation prevents the expression of the corresponding gene product, wherein the first deletion is flanked by nucleotides 1-136 and nucleotides 137-232 of SEQ ID NO: 7, wherein the second deletion is flanked by nucleotides 1-289 and nucleotides 290-518 of SEQ ID NO: 8, and wherein the third deletion is flanked by nucleotides 1-200 and nucleotides 201-333 of SEQ ID NO: 9.

2. A composition comprising an isolated bacterium, wherein the isolated bacterium comprises a mutation to each of three NiFe hydrogenase genes present in the genome of the isolated bacterium, wherein each mutation prevents expression of the corresponding gene product, and wherein the isolated bacterium is *S. typhimurium* strain JSG 321, deposited with the American Type Culture Collection depository.

3. *S. typhimurium* strain JSG 321 deposited with the American Type Culture Collection depository under Accession No: PTA-6556.

* * * * *

UNITED STATES PATENT AND TRADEMARK OFFICE

CERTIFICATE OF CORRECTION

PATENT NO. : 7,919,081 B2
APPLICATION NO. : 10/591203
DATED : April 5, 2011
INVENTOR(S) : Maier et al.

It is certified that error appears in the above-identified patent and that said Letters Patent is hereby corrected as shown below:

On the Title page under Item (73) Assignee:

add

The Ohio State University
1960 Kenny Road
Columbus, Ohio 43065

Signed and Sealed this
Sixteenth Day of August, 2011

David J. Kappos
*Director of the United States Patent and Trademark Office*